(12) United States Patent
Shah et al.

(10) Patent No.: US 11,092,577 B2
(45) Date of Patent: Aug. 17, 2021

(54) POLAR PESTICIDE DETERMINATION USING CHROMATOGRAPHY

(71) Applicant: Waters Technologies Corporation, Milford, MA (US)

(72) Inventors: Dimple D. Shah, Milford, MA (US); Jacob N. Fairchild, Upton, MA (US); Euan Ross, Dundee (GB); Benjamin Wuyts, Herentals (BE)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 257 days.

(21) Appl. No.: 15/914,428

(22) Filed: Mar. 7, 2018

(65) Prior Publication Data

US 2018/0259494 A1 Sep. 13, 2018

Related U.S. Application Data

(60) Provisional application No. 62/468,700, filed on Mar. 8, 2017, provisional application No. 62/582,237, filed on Nov. 6, 2017.

(51) Int. Cl.
*G01N 30/88* (2006.01)
*G01N 30/72* (2006.01)
(Continued)

(52) U.S. Cl.
CPC ........ *G01N 30/482* (2013.01); *G01N 30/72* (2013.01); *G01N 30/74* (2013.01);
(Continued)

(58) Field of Classification Search
CPC ...... G01N 30/482; G01N 30/88; G01N 30/72; G01N 30/74; G01N 30/8631;
(Continued)

(56) References Cited

U.S. PATENT DOCUMENTS

| 4,017,528 A | 4/1977 | Unger et al. |
| 4,049,496 A * | 9/1977 | Henry ............... A61K 38/45 |
| | | 435/17 |

(Continued)

FOREIGN PATENT DOCUMENTS

| EP | 3184157 A1 | 6/2017 |
| WO | 2016/026286 A1 | 2/2016 |

OTHER PUBLICATIONS

Cojocariu, Christian, et al. "Three-Fold Increase in Productivity for Pesticide Residue Analysis in Baby Food Using Fast Triple Quadrupole GC-MS/MS," Thermo Scientific, 2016. (Year: 2016).*

(Continued)

*Primary Examiner* — Lyle Alexander
*Assistant Examiner* — Michael Paul Shimek
(74) *Attorney, Agent, or Firm* — Womble Bond Dickinson (US) LLP; Deborah M. Vernon; Scott Raymond Breining

(57) ABSTRACT

The present disclosure relates to the determination of pesticides, e.g., polar pesticides, in a sample using chromatography. The present disclosure can provide direct analysis of polar pesticides, including anionic polar pesticides, using high performance liquid chromatography. The polar pesticides are sufficiently retained and resolved to allow for multiple polar pesticide determinations in a single analysis.

20 Claims, 34 Drawing Sheets

(51) Int. Cl.
    G01N 30/74      (2006.01)
    B01J 20/281     (2006.01)
    G01N 30/86      (2006.01)
    G01N 33/18      (2006.01)
    G01N 30/02      (2006.01)
(52) U.S. Cl.
    CPC ......... G01N 30/8631 (2013.01); G01N 30/88 (2013.01); G01N 2030/027 (2013.01); G01N 2030/884 (2013.01); G01N 2033/184 (2013.01)
(58) Field of Classification Search
    CPC ....... G01N 2033/184; G01N 2030/884; G01N 2030/027
    See application file for complete search history.

(56) References Cited

U.S. PATENT DOCUMENTS

| | | | |
|---|---|---|---|
| 6,528,167 B2 | 3/2003 | O'Gara | |
| 6,686,035 B2 | 2/2004 | Jiang et al. | |
| 7,175,913 B2 | 2/2007 | O'Gara | |
| 2006/0144770 A1* | 7/2006 | Granger | B01J 19/0093 210/198.2 |
| 2011/0301346 A1* | 12/2011 | Angeli | B01D 15/325 544/178 |
| 2014/0157871 A1* | 6/2014 | Dubant | G01N 30/06 73/23.41 |

OTHER PUBLICATIONS

Hao, Chunyan, et al. "Direct aqueous determination of glyphosate and related compounds by liquid chromatography/tandem mass spectrometry using reversed-phase and weak anion-exchange mixed-mode column," Journal of Chromatography A, vol. 1218, Iss. 33, p. 5638-5643, Aug. 19, 2011. (Year: 2011).*

International Search Report and Written Opinion relating to International Application No. PCT/IB2018/051486, 15 Pages, dated Jun. 13, 2018.

Chunyan, et al., "Direct Aqueous Determination of Glyphosate and Related Compounds by Liquid Chromatography/Tandem Mass Spectrometry using Reversed-Phase and Weak Anion-Exchange Mixed-Mode Column," Journal of Chromatography A, 1218 (2011) 5638-5643.

Masia, et al., "Determination of Pesticides and Veterinary Drug Residues in Food by Liquid Chromatography—Mass Spectrometry: A Review," Analytica Chimica Acta 936 (2016) 40-61.

Wuyts, et al., "Highly Sensitve Analysis of Polar Pesticides in Food Matrices on the Xevo TQ-XS," Waters Corporation Technology Brief, (Oct. 2016).

Steinborn, et al., "Determination of Glyphosate Levels in Breast Milk Samples from Germany by LC-MS/MS and GC-MS/MS," J. Agric. Food Chem. (2016), 64, 1414-1421.

Chamkasem, et al., "Direct Determination of Glyphosate, Glufosiante, and Ampa in Soybean and Corn by Liquid , Chromatography/Tandem Mass Spectrometry," Analytical and Bioanalytical Chemistry, Research Paper (2016).

Pihlström, et al., Revisions to Document N° Sante /2013 / 12571 titled, "Analytical Quality Control and Method Validation Procedures for Pesticide Residues Analysis in Food and Feed," 48 Pages, Jan. 1, 2016.

Waters Corporation, "Controlling Contamination in LC/MS Systems— Best Practices," 715001307 Rev. G, 33 Pages, (2016).

"EPA Method 547: Determination of Glyphosate in Drinking Water by Direct-Aqueous Injection HPLC, Post-Column Derivatization and Fluorescence Detection." Waters Application Notes 720006246en. (2008).

"Guidance document on analytical quality and method validation procedures for pesticide residue analysis in food and feed." Sante, Commission of the European Communities (2015) Document No. Sante/11945/2015. Rev. 0, implemented by Jan. 1, 2016.

"Ion Chromatography." Thermo Fisher Scientific. Retrieved on Jul. 24, 2019. <https://www.mayomedicallaboratories.com/test-catalog/Overview/80289>.

"Test ID: MMAS: Methylmalonic Acid (MMA), Quantitative, Serum." Mayo Clinic Laboratories. Retrieved on Jul. 24, 2019. https://www.mayocliniclabs.com/test-catalog/Overview/80289.

"Water quality—Determination of glyphosate and AMPA—Method using high performance liquid chromatography (HPLC) with tandem mass spectrometric detection." International Standard: ISO 16308:2014(E). Sep. 15, 2014.

Anastassiades et al. "Quick Method for the Analysis of Numerous Highly Polar Pesticides in Foods of Plant Origin via LC-MS/MS involving Simultaneous Extraction with Methanol (QuPPE-Method)." Version 9.3 (Aug. 2017, Document History, see p. 73). EURL-SRM: EU Reference Laboratories for Residues of Pesticides: Single Residue Methods.

Bajad et al. "Separation and quantitation of water soluble cellular metabolites by hydrophilic interaction chromatography-tandem mass spectrometry." J. Chromatogr. A. 1125(2006):76-88.

Fiori et al. "Cellular and mitochondrial determination of low molecular mass organic acids by LC-MS/MS." J. Pharma. Biomed. Anal. 150(2018): 33-38.

Russell et al. "Analysis of Polar Ionic Pesticides by IC-MS: Possible Solution to a Long-Standing Problematic Analysis?" Thermo Scientific. 2017. <http://tools.thermofisher.com/content/sfs/posters/PO-72369-IC-MS-Polar-Ionic-Pesticides-ASMS2017-P072369-EN.pdf>.

Gritti et al. "Adsorption behaviors of neutral and ionizable compounds on hybrid stationary phases in the absence (BEH-C18) and the presence (SH-C18) of immmobile surface charges." J. Chromatogr. A. 1282(2013): 58-71.

Gritti et al. "Effect of the ionic strength on the adsorption process of an ionic surfactant onto a C18-bonded charged surface hybrid stationary phases at low pH." J. Chromatogr. A. 1282(2013): 46-57.

Gritti et al. "Effect of the pH and the ionic strength on overloaded band profiles of weak bases onto neutral and aharged surface hybrid stationary phases in reversed-phase liquid chromatography." J. Chromatogr. A. 1282(2013): 113-126.

Hinder et al. "Decreased glycolytic and tricarboxylic acid cycle intermediate coincide with peripheral nervous system oxidative stress in a murine model of type 2 diabetes." J. Endocrinol. 216(2013): 1-11.

Iraneta et al. "A Review of Waters Hybrid Particle Technology. Part 3. Charged Surface Hybrid (CSH) Technology and Its Use in Liquid Chromtography." Waters white paper 720003929en. 2011.

Lu et al. "Metabolomic Analysis via Reversed-Phase Ion-Pairing Liquid Chromatography Coupled to a Stand Alone Orbitrap Mass Spectrometer." Anal. Chem. 82(2010): 3212-3221.

Luo et al. "Simultaneous determination of multiple intracellular metabolites in glycolysis, pentose phosphate pathway and tricarboxylic acid cycle by liquid chromatography-mass spectrometry." J. Chromtogr. A. 1147(2007): 153-164.

Mallet. "Analysis of Glysophase, Glufosinate, and AMPA in Tap and Surface Water Using Open-Architecture UPLC with 2D-LC Technology." Waters Application Notes 720005169en. (2014).

Melo et al. "Brief Review Analytical Methods for the Determination of Glyphosate." MOJ Toxicol. 4.2(2018): 00088.

Michopoulos et al. "Targeted profiling of polar intracellular metabolites using ion-pair-high performance liquid chromatography and -ultra high performance liquid chromatography coupled to tandem mass spectrometry: Applications to serum, urine and tissue extracts" J. Chromatogr. A. 1349(2014): 60-68.

Neue et al. "Adsorption of cations onto positively charged surface mesopores." J. Chromatogr. A. 1318(2013): 72-83.

Novakova et al. "Evaluation of new mixed-mode UHPLC stationary phases and the importance of stationary phase choice when using low ionic-stregnth mobile phase additives." Talanta. 93(2012): 99-105.

Rustin et al. "Inborn errors of the Krebs cycle: a group of unusual mitochondrial diseases in human." Biochim. Biophys. Acta. 1361(1997): 185-197.

(56) References Cited

OTHER PUBLICATIONS

Smith et al., ed. "March's Advanced Organic Chemistry." Seventh Edition. Hoboken, NJ: John Wiley & Sons. (2007): 1-2357.

Tan et al. "Derivatization of the tricarboxylic acid intermediates with O-benzylhydroxylamine for liquid chromatography-tandem mass spectrometry detection." Anal. Biochem. 465(2014): 134-147.

Van Genderen-de Kloe et al. "Analysis of Glyphoste, AMPA, and Glufosinate in Water Using UPLC-MS/MS." Waters Application Notes 720006246en. (2018).

Winfield et al. "Method 547: Determiantion of Glyphosate in Drinking Water by Direct-Aqueous Injection HPLC, Post-Column Derivatization and Fluorescence Detection." U.S. Environmental Protection Agency: Enivironmental Monitoring Systems Laboratory, Office of Research and Development. Jul. 1990.

Yang et al. "Analysis of Glyphosate and AMPA in Environmental Water by Ion Chromatography Electrospray Tandem Mass Spectrometry (IC-ESI-MS/MS)." Thermo Scientific: Application Note: 491. 2010.

Yoshioka et al. "Rapid determination of glyphosate, glufosinate, bialaphos, and their major metabolites in serum by liquid chromatography-tandem mass spectrometry using hydrophilic interaction chromatography." J. Chromatogr. A. 1218(2011):3675-3680.

* cited by examiner

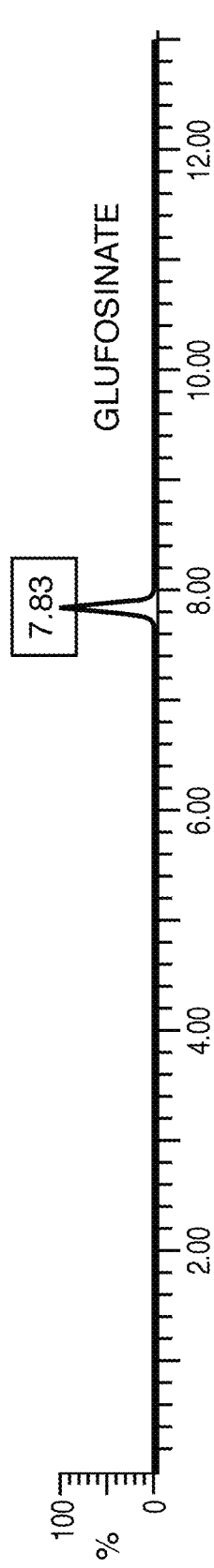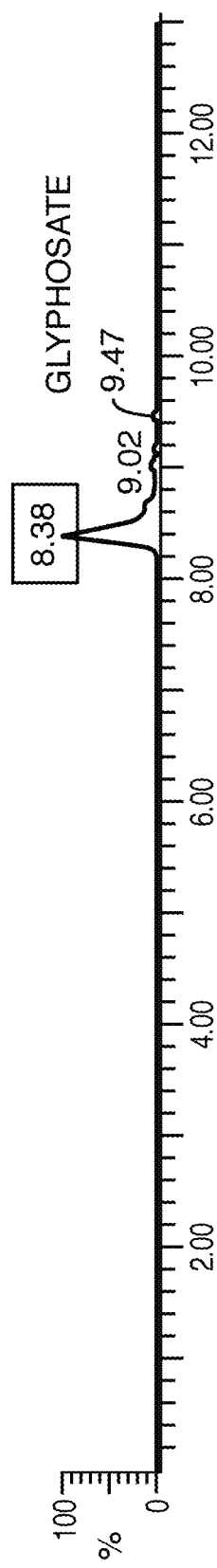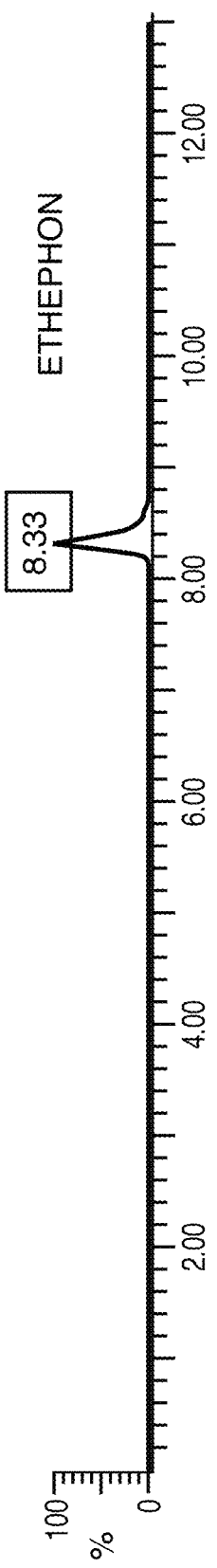

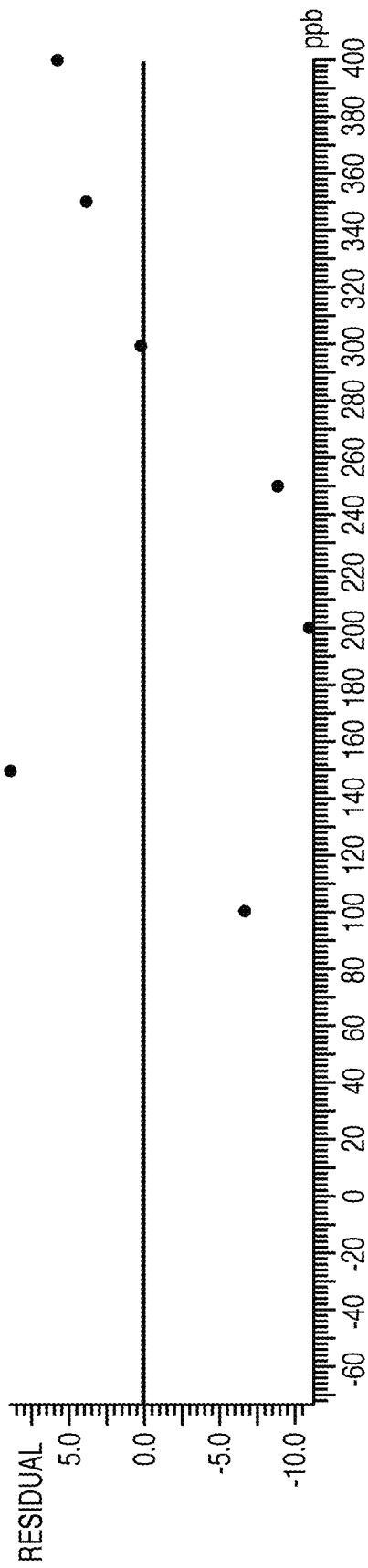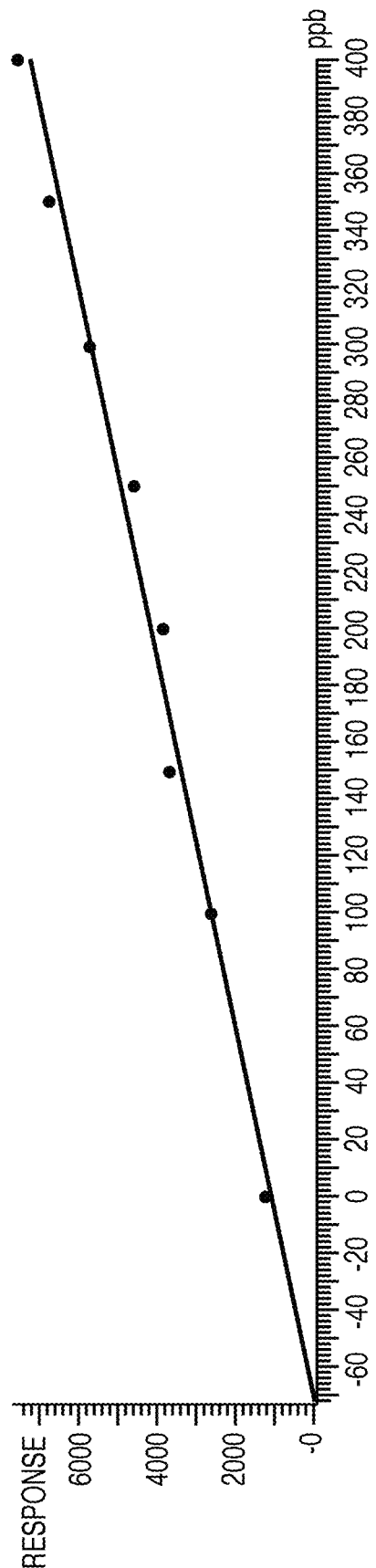
FIG. 7A
FIG. 7B

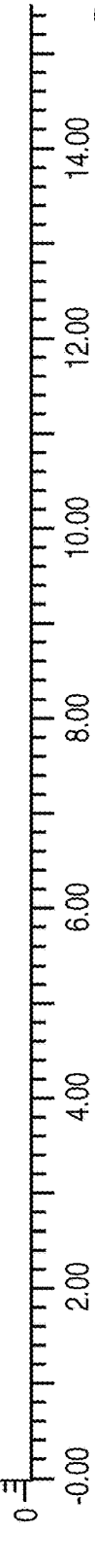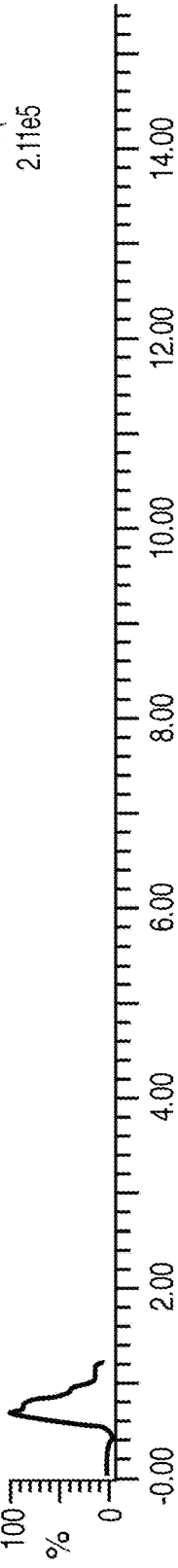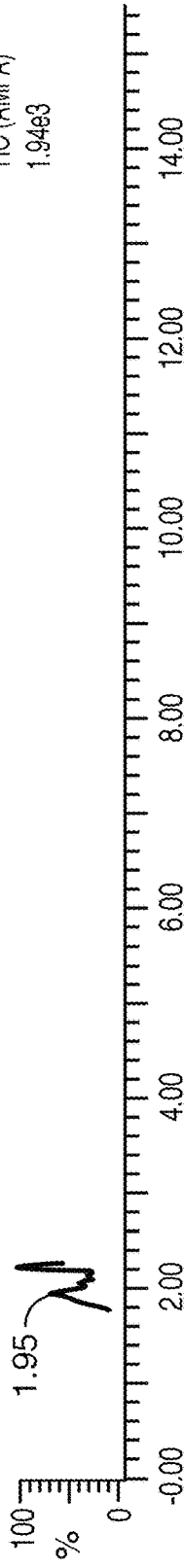

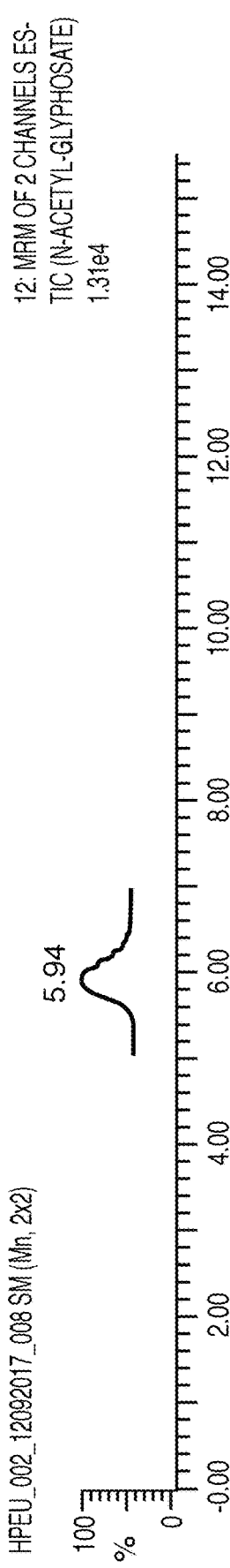
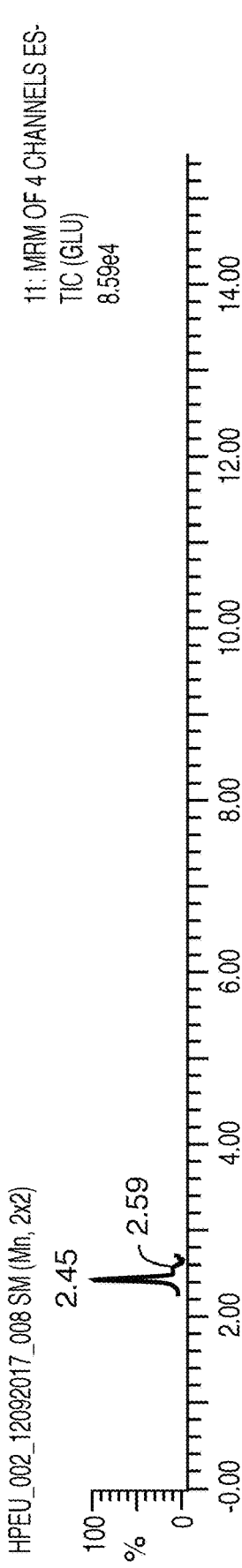
FIG. 12A
FIG. 12B
FIG. 12C

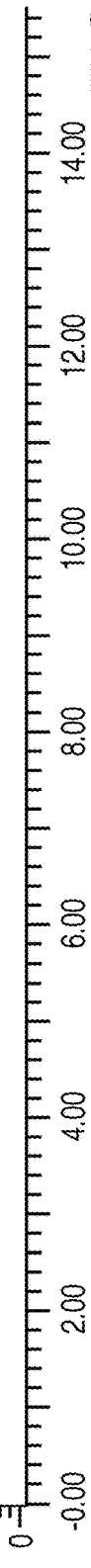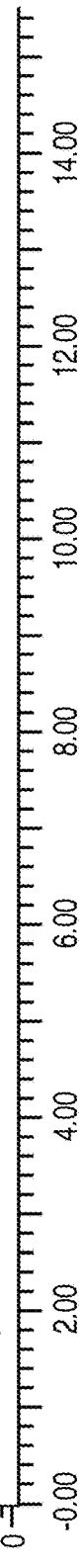
FIG. 12G
FIG. 12H
FIG. 12I

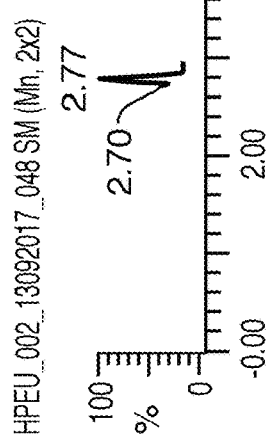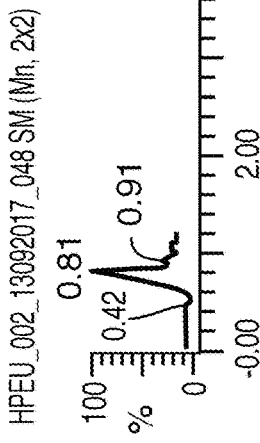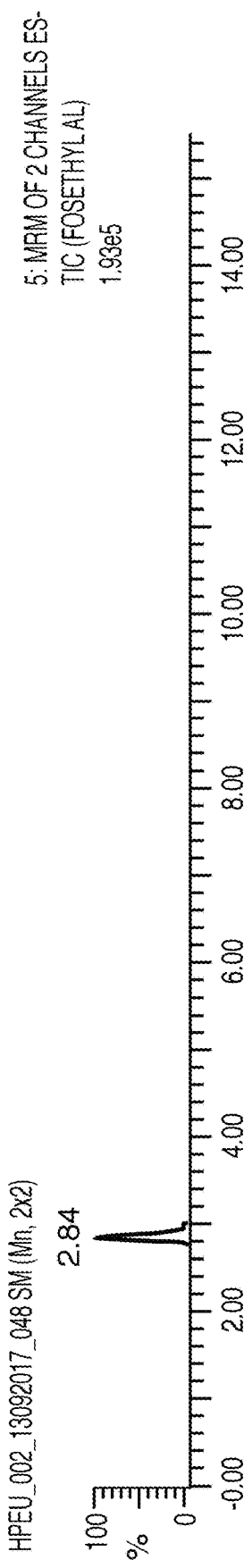

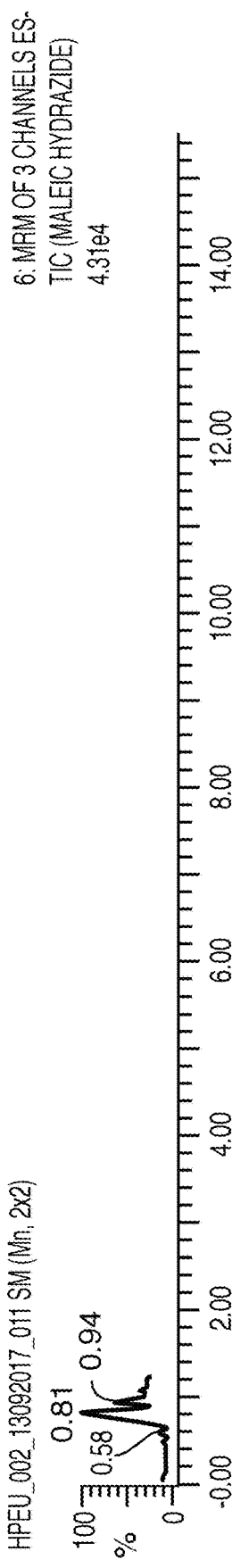
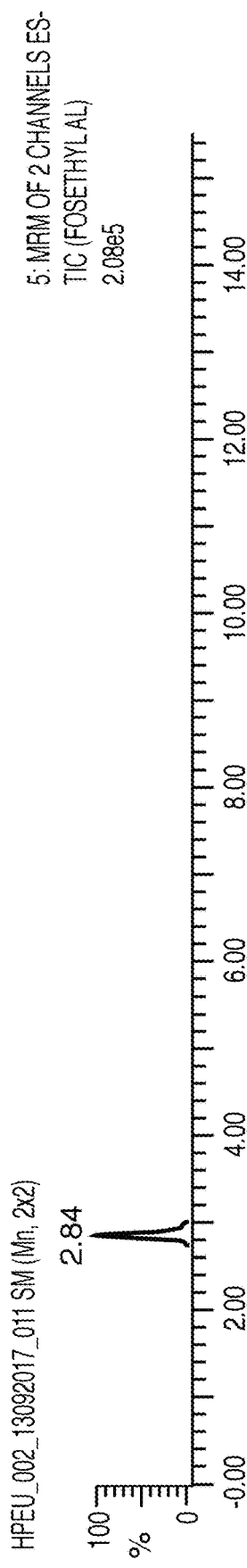
FIG. 14G
FIG. 14H
FIG. 14I

POLAR PESTICIDE DETERMINATION USING CHROMATOGRAPHY

CROSS REFERENCE TO RELATED APPLICATIONS

This application claims benefit of and priority to U.S. Provisional Application Nos. 62/468,700 entitled "Polar Pesticide Determination Using Chromatography" filed Mar. 8, 2017, and 62/582,237 entitled "Polar Pesticide Determination Using Chromatography" filed Nov. 6, 2017, the contents of each of which are incorporated herein by reference in their entirety.

FIELD OF THE TECHNOLOGY

The present disclosure relates to the determination of pesticides, e.g., polar pesticides, in a sample using chromatography. The present disclosure can provide direct analysis of polar pesticides, including anionic polar pesticides, using for example, liquid chromatography, and/or high performance liquid chromatography.

BACKGROUND

Pesticide residues resulting from the use of plant protection products on crops that are used for food or feed production pose a risk factor for public health. A comprehensive legislative framework has been established in each country which defines rules for the approval of active substances used in plant protection products, like pesticides. These rules regulate the use of plant protection products and set maximum amounts of residues permitted in food. Residue definitions are set during the evaluation process of the active substance, which may include relevant metabolites and other transformation products. Food surveillance testing programs check for compliance with maximum residue limits (MRLs), assess dietary exposure, and check for use of unauthorized pesticides. The food industry also undertakes testing of ingredients and finished products for due diligence, or product release purposes. Samples from the environment (e.g. water) and biological fluids are also tested to determine the level of pollution and human exposure, respectively. Some of the polar pesticides are amongst the most commonly used plant protection products so there is a need for robust methods with which to monitor food and the environment for residues to ensure compliance with local statutory maximum permitted limits and to evaluate exposure and human health.

SUMMARY

The present disclosure relates to the determination of pesticides, e.g., polar pesticides, in a sample using chromatography. The present disclosure can provide direct analysis of polar pesticides, including anionic polar pesticides, using for example liquid chromatography, high performance liquid chromatography and/or ultra high performance liquid chromatography.

In one embodiment, the present disclosure relates to a chromatography method for determining (e.g., separating and detecting) at least one polar pesticide and/or metabolite, the method including obtaining a sample containing at least one polar pesticide and/or motabolite in a sample matrix, introducing the sample to a chromatography system including a column having a stationary phase material contained inside the column, flowing the sample with a mobile phase eluent through the column, wherein the at least one polar pesticide and/or metabolite is substantially resolved, retained or both, and detecting the at least one polar pesticide and/or metabolite using a detector.

The sample can contain multiple polar pesticides and/or metabolites, such as 2 or more, wherein the polar pesticides and/or metabolites are substantially resolved, e.g., have a resolution greater than about 1. For example, the at least two polar pesticides can be isobaric polar pesticides. The method can further include extracting the polar pesticide(s) and/or metabolite(s) from the sample matrix before introducing the extracted sample to the chromatography system. The retention time for the polar pesticide(s) and/or metabolite(s) can be at least 1.5× the retention time of the column void volume. The repeatability of multiple analyses of the same sample (or standard) as measured by peak area has a relative standard deviation (RSD) less than about 20%.

In another embodiment, the present disclosure relates to a kit. The kit can include a chromatography system having a column and a detector applicable to determining (e.g., retaining, separating, detecting) polar pesticides and/or metabolites. The column can have a stationary phase material contained inside the column. The kit can also include instructions for obtaining a sample containing at least one polar pesticide and/or metabolite in a sample matrix. The kit can also include instructions for introducing the sample to the chromatography system. The kit can also include instructions for flowing the sample with a mobile phase eluent through the column, wherein the at least one polar pesticide and/or metabolite is substantially resolved, retained, or both. Finally, the kit can also include instructions for detecting the at least one polar pesticide using a detector.

At least one polar pesticide and/or metabolite can be selected from the group consisting of Ethephon, Glufosinate-ammonium, Glyphosate, Fosetyl-aluminium, Phosphonic acid, Maleic hydrazide, Perchlorate, Chlorate, Cyromazine, Amitrole, Daminozide, Ethylenethiourea, Propylenethiourea, Chlormequat, Mepiquat, Diquat, Paraquat, and metabolites thereof, and combinations thereof.

The stationary phase material can include inorganic/organic hybrid particles and can be configured to operate under a pressure at or above 1,000 psi. The stationary phase material can include an amine functional group. The stationary phase material can include a diethyl amine functional group, a 2-picolylamine functional group, a 2-ethylpyridine functional group, or a 4-ethylpyridine functional group. The stationary phase material can include a diol functional group. The stationary phase material can include a first amine functional group and a second diol functional group, wherein the ratio of amine functional group to diol functional group is between about 0.01:1 and 1:1.

The mobile phase eluent can include acetonitrile, buffer or combinations thereof. The mobile phase eluent can have a flow rate between 0.2 and 1.0 mL/min. The mobile phase eluent can include organic and aqueous solvents containing buffer, or combinations thereof, and the at least one polar pesticide or metabolite can be eluted using a gradient elution, the elution including a gradient of a first solvent comprising an aqueous solvent and a second solvent including an organic solvent.

The column temperature can be between 30 and 60° C.

The retention time for the at least one polar pesticide or metabolite determined can be at least twice the retention time corresponding to the void volume of the column.

The method repeatability of performing the method at least 10 times using the same chromatography system measuring peak area can have an RSD less than about 20%, wherein the sample is a solution of polar pesticide or metabolite reference standards.

The sample can contain at least 2 polar pesticides or metabolite which are substantially resolved, and wherein the substantially resolved at least 2 polar pesticides or metabolites can have a resolution greater than 1.

The detector can be selected from the group consisting of a UV/VIS detector, PDA detector, fluorescence detector, mass spectrometer, refractive index detector, evaporative light scattering detector and a charged aerosol detection.

The present disclosure provides a number of advantages over current systems and methodology. For example, current chromatographic methods can use ion pair reagents or derivatization with reversed-phase chromatography using (e.g., OPA or FMOC reagents). There are methods that use porous graphitized carbon, ion chromatography, hydrophilic interaction chromatography, or mixed mode chromatography. These methods, however, have limitations. They require a number of different single residue methods to cover the full analytical scope, specialized equipment or derivatization. Some methods have issues with robustness, or ion suppression from mobile phase additives, or insufficient retention of some compounds, or have operating backpressure limits which restrict the useable flow rate and can cause blockages. Also, these methods are not amendable to all pesticides, such as those that are polar, highly polar, ionic in nature, or combinations thereof. These pesticides are often hard to extract, retain and separate on traditional chromatography systems.

The present disclosure relates to the use of chromatography apparatus and methodology for the determination of these polar pesticides in a cost-effective and efficient manner. The present methodology provides improved chromatographic performance, including sufficient retention of a wide range of polar pesticides and metabolites, in a single analysis, without resorting to derivatization or specialized equipment or conditions. The present methodology is robust and easily implemented in routine testing laboratories. It is compatible with existing conventional HPLC and UPLC instrumentation. The present methodology meets most regulatory requirements for pesticide analysis, including the European Commission criteria as published in Document No. SANTE/11945/2015 titled "Analytical Quality Control and Method Validation Procedures for Pesticide Residues Analysis in Food and Feed."

BRIEF DESCRIPTION OF THE DRAWINGS

The invention will be more fully understood from the following detailed description taken in conjunction with the accompanying drawings, in which:

FIGS. 3A-3I are chromatograms showing baseline separation of glufosinate (FIG. 3A), glyphosate (FIG. 3B), ethephon (FIG. 3C), maleic hydrazide (FIG. 3D), AMPA (FIG. 3E), fosetyl-aluminium (FIG. 3F), perchlorate (FIG. 3G), chlorate (FIG. 3H) and phosphonic acid (FIG. 3I) according to an illustrative embodiment of the technology.

FIGS. 7A and 7B are standard addition plots quantifying incurred residue of maleic hydrazide in onion to 0.072 mg/kg, according to an illustrative embodiment of the technology.

FIGS. 11A-11M are chromatograms showing baseline separation of N-Acetyl-Glufosinate (FIG. 11A), N-Acetyl-Glyphosate (FIG. 11B), glufosinate (FIG. 11C), glyphosate (FIG. 11D), MPPA (FIG. 11E), ethephon (FIG. 11F), ethephon hydroxyl (FIG. 11G), maleic hydrazide (FIG. 11H), AMPA (FIG. 11I), fosetyl-aluminium (FIG. 11J), perchlorate (FIG. 11K), chlorate (FIG. 11L) and phosphonic acid (FIG. 11M) for QuPPE method for onion extract, according to an illustrative embodiment of the technology.

FIGS. 12A-12M are chromatograms showing baseline separation of N-Acetyl-Glufosinate (FIG. 12A), N-Acetyl-Glyphosate (FIG. 12B), glufosinate (FIG. 12C), glyphosate (FIG. 12D), MPPA (FIG. 12E), ethephon (FIG. 12F), ethephon hydroxyl (FIG. 12G), maleic hydrazide (FIG. 12H), AMPA (FIG. 12I), fosetyl-aluminium (FIG. 12J), perchlorate (FIG. 12K), chlorate (FIG. 12L) and phosphonic acid (FIG. 12M) for modified QuPPE method for onion extract, according to an illustrative embodiment of the technology.

FIGS. 13A-13M are chromatograms showing baseline separation of N-Acetyl-Glufosinate (FIG. 13A), N-Acetyl-Glyphosate (FIG. 13B), glyphosate (FIG. 13C), glufosinate (FIG. 13D), MPPA (FIG. 13E), ethephon (FIG. 13F), ethephon hydroxyl (FIG. 13G), maleic hydrazide (FIG. 13H), fosetyl-aluminium (FIG. 13I), AMPA (FIG. 13J), perchlorate (FIG. 13K), chlorate (FIG. 13L) and phosphonic acid (FIG. 13M) for QuPPE method for spinach extract, according to an illustrative embodiment of the technology.

FIGS. 14A-14M are chromatograms showing baseline separation of N-Acetyl-Glufosinate (FIG. 14A), N-Acetyl-Glyphosate (FIG. 14B), glyphosate (FIG. 14C), glufosinate (FIG. 14D), MPPA (FIG. 14E), ethephon (FIG. 14F), ethephon hydroxyl (FIG. 14G), maleic hydrazide (FIG. 14H), fosetyl-aluminium (FIG. 14I), AMPA (FIG. 14J), perchlorate (FIG. 14K), chlorate (FIG. 14L) and phosphonic acid (FIG. 14M) for modified QuPPE method for spinach extract, according to an illustrative embodiment of the technology.

DETAILED DESCRIPTION

The present disclosure relates to the determination of pesticides, e.g., polar pesticides, in a sample using chromatography. The present disclosure can provide direct analysis of polar pesticides, including anionic polar pesticides, using high performance liquid chromatography.

As used herein, the term "isobaric" refers to pesticides having the same, or substantially the same, Multiple Reaction Monitoring (MRM) transitions.

As used herein, the term "repeatability" refers to the determination, expressed as the RSD, of multiple measurements of a solution of reference standards on the same system under the same conditions.

As used herein, the term "resolution" refers to the measure of how well two peaks are separated. Resolution can be determined by $R=(Tr2-Tr1)/(0.5\times(Tw1+Tw2))$, wherein Tr is the retention time of either peak 1 or peak 2, and Tw is the peak width at half height for peak 1 and peak 2.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

Figure 1:
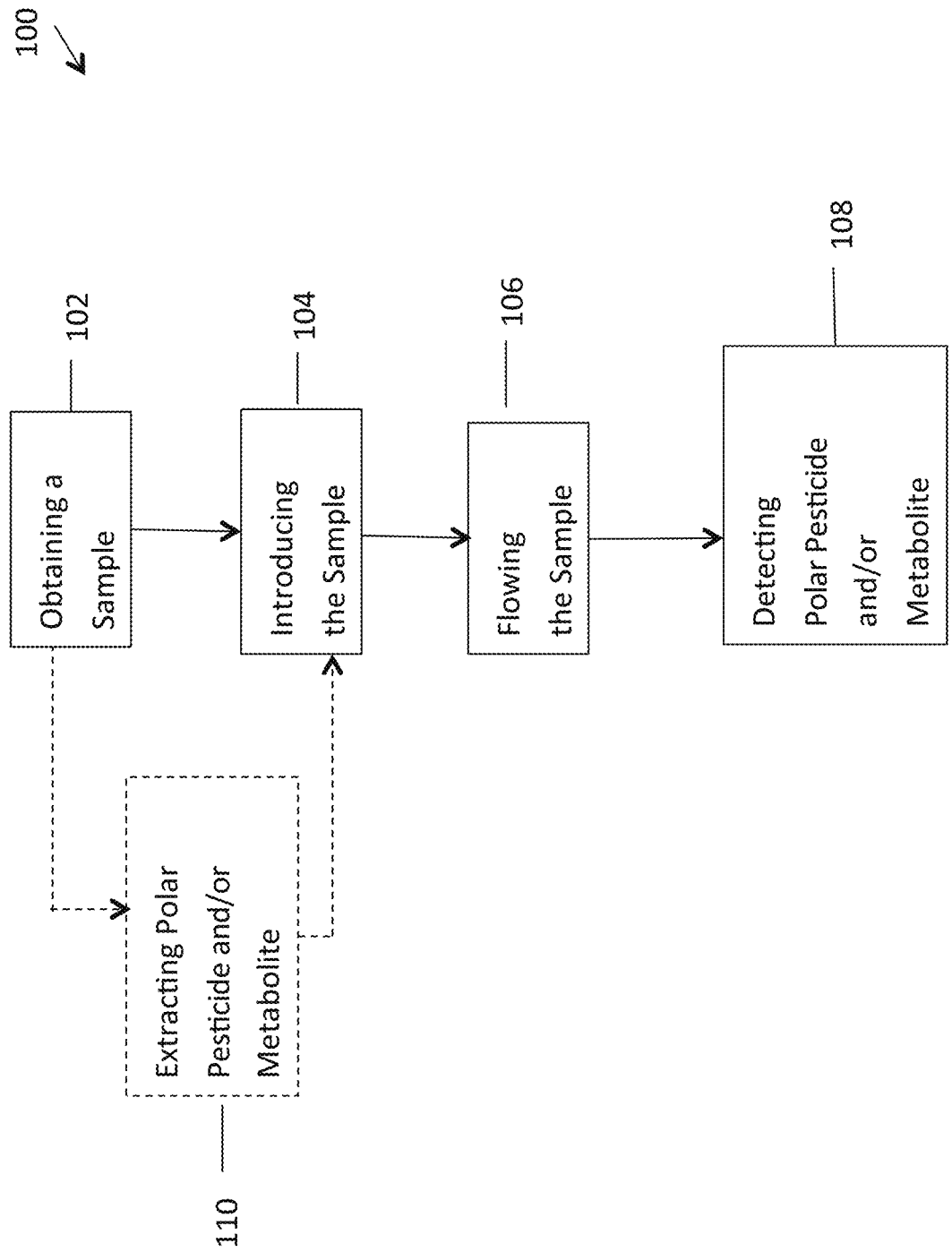
FIG. 1 is a flow chart of a method for determining at least one polar pesticide or metabolite, according to an illustrative embodiment of the technology.

In one embodiment, the present disclosure relates to a chromatography method 100 for determining polar pesticides or metabolites. Referring to FIG. 1, the method 100 includes obtaining a sample 102 containing at least one polar pesticide or metabolite in a sample matrix, introducing the sample 104 to a chromatography system including a column having a stationary phase material contained inside the column, flowing the sample 106 with a mobile phase eluent through the column, wherein the at least one polar pesticide or metabolite is substantially resolved, retained or both, and detecting the at least one polar pesticide or metabolite 108 using a detector. In some embodiments of the technology, the method 100 includes extracting the at least one polar pesticide or metabolite 110 from the sample matrix before introducing the extracted sample 104 to the chromatography system Polar pesticides or metabolites (herein referred to simply polar pesticides) can be difficult to retain and separate using chromatography. There are issues with current methods for the determination of polar pesticides. Polar pesticides can elute together at or near the void volume of the column. When retained, the polar pesticides can still be difficult to resolve into individual peaks. In some instances, one or more critical pairs of polar pesticides cannot be resolved in a single analysis. Known pesticide chromatography methods also have poor repeatability and high back pressures, even when extracted from the sample matrix. Current methods use FMOC derivatization with a C18 column (i.e., needs extra steps). Others use ion pair reagents with a C18 column, but this can lead to contamination of LC system and ion suppression leading to a reduction in sensitivity and has restricted analytical scope. PGC can be used but it needs considerable priming with the matrix of interest to provide consistent results so not suitable for analysis of batches of mixed origin, relies on the use of stable isotope analogues to normalize variability. IC can also be used, but the columns are limited to larger particle size and relies on the use of reagents that need specialist equipment or which suppress the response and need relatively long run times when scope of analysis is broad. HILIC columns have been used, but they are not very robust and are limited by the extract solvent that can be injected. Overall, these methods make it difficult to develop methods and maintain chromatographic performance for polar pesticides. Mixed mode columns have also been used, but they do not provide suitable chromatographic performance for all polar pesticides and some columns have limited backpressure. The present methodology addresses one or more of these issues. The methodology can retain and separate one or more critical pairs of polar pesticides for both identification and quantification with improved repeatability, with or without extraction, and at high pressures.

The present methodology is compatible with existing extraction methods such as QuPPe and aqueous extraction methods. It is able to retain and separate a wide range of polar pesticides. For example, the methodology can produce high efficiency separations using small particle size stationary phases, e.g., 1.7 µm particle size, and cope with backpressure generated at typical UPLC flow rates. In some embodiments, the methodology can have sufficient retention of all polar pesticides and can be able to separate isobaric polar pesticides, e.g., AMPA and fosetyl-aluminium. The method can maintain efficient separations over an extended period (400 injections) and is compatible with conventional HPLC/UPLC systems, such that there is no need for costly specialist equipment. It is compatible with MS, such that there is no need for MS incompatible solvents, mobile phase buffers or ion pair reagents. The analysis can be without modification of the analytes or the need for derivatization or ion pair reagents.

The sample can be any sample containing polar pesticides applicable to the current methodology. The sample can be generated from a food, plant, animal or environmental sources (e.g., soil, sediment, water, air, biological fluids or related source). The sample can be, or can be obtained from, water, juices, alcoholic beverages, beer, dry goods, grains, starches, cereal, fresh meat, frozen meat, processed meats products, e.g., sausage, cold cuts, spices, chocolate, pet food, whey powder, frozen produce, fresh produce, eggs, vitamins, oils, fats, fruits, cannabis/cannabinoids or combinations thereof. The sample can be obtained by direct sampling, e.g., taking a neat sample, or by washing or rinsing the sample source. The neat sample, or the wash/rinse sample can be tested by the present methodology.

The sample matrix can include one or more of the following components as provided in the following categories. Food includes foodstuffs, such as high water content (e.g., fruit, vegetables, forage/fodder crops, fresh fungi, potable water and beverages); high acid, high water content (e.g., citrus fruit and juices, small fruit/berries, other acidic fruits); high sugar, low water content (e.g., honey, dried fruit); very high oil content, low water content (e.g., tree nuts, oil seeds and associated pastes and oils); high oil content, intermediate water content (e.g., oily fruits and associated products); high starch and/or protein content, low water and fat content (e.g., dry legume vegetables/pulses, cereal grain and products. For example, orange juice, spinach, onion, barley, apple juice, tomato juice, beer, wheat, honey, and/or lentils can be analyzed with the apparatus and methodology of the present disclosure. Those not fitting above categories (e.g., hops, cocoa beans and products thereof, coffee, tea and spices); meat and seafood (e.g., red meat, poultry meat, offal, fish and crustaceans); milk and milk products (e.g., milk, cheese, yogurt and cream) and eggs. The sample must be extracted prior determination. Each of these matrix components can be contained in the sample matrix at individual amounts including about, or less than about, 1 ppb, 2, 5, 10, 20, 50, 100, 200, 500, 1000 ppb, 2 ppm, 5, 10, 20, 50, 100, 200, 500, 1000 ppm, 2 ppt, 5, 10, 20, 50, 90, 98, 99 or 100 ppt. These values can be used to define a range, such as from about 2 ppb to about 20 ppm. In one embodiment, the sample matrix can contain about or more than about 1000 ppm protein. In another embodiment, the sample matrix can contain about or more than about 1000 ppm fat.

The sample matrix can also be characterized by ionic strength. The ionic strength of the sample matrix can be about, more than about, or less than about, 0.1 mM, 0.2, 0.5, 1, 2, 5, 10, 20, 50, 100, 200, 500, 1000, 2000 or about 5000 mM. These values can be used to define a range, such as from about 2 mM to about 50 mM.

The apparatus and methodology of the present disclosure is robust and rugged. In some embodiments, the methodology can determine polar pesticides in sample matrices that have not been extracted or filtered. The sample matrix can have one or more components, or ionic strength as described herein. The system is robust and rugged, in part, because of the column technology and the ability of the system and column to function at high pressure. The presence of matrix components which can cause higher system pressures can be tolerated by the system of the present disclosure.

In other embodiments, the sample can be extracted to isolate polar pesticides (e.g., remove or reduce components) from the sample matrix. The method can further include an extraction method to purify, concentrate, or both the polar pesticide(s) from the sample (see, 110 of FIG. 1). Numerous extraction techniques can be used including QuPPe (Quick Polar Pesticides Method) and modifications thereof, and similar aqueous extraction methods.

The sample can contain at least one polar pesticide. The sample can also contain more than one polar pesticide. In some embodiments, the sample contains at least 2, 3, 4, 5, 6, 7, 8, 9, 10, 11, 12, 13, 14, 15, 16, 17, 18, 19, 20 or more polar pesticides. These values can also define a range, such as from about 2 and to about 9 polar pesticides. For samples having at least two or more polar pesticides, the methodology can substantially resolve and retain at least two or more of the polar pesticides from each other.

The present methodology is applicable to a wide range of polar pesticides. The polar pesticide(s) can be selected from the group consisting of 1,3-dichloropropene, 2-hydroxyethyl phosphonic acid (HEPA), 3-methylphosphinicopropionic acid (MPPA), aldicarb, aldrin, alpha-cypermethrin, aminomethylphosphonic acid (AMPA), amitraz, amitrole, azinphosethyl, azinphos-methyl, benfuracarb, beta-cyfluthrin, beta-cypermethrin, bifenthrin, carbendazim, carbofuran, carbosulfan, chlorate, chlormequat, chloropicrin, chlorpyrifos, chlorpyrifos-methyl, cyfluthrin, cyhalothrin, cypermethrin, cyromazine, daminozide, DDT, diazinon, dichlorvos, difenoconazole, dimethoate, diquat, ethephon, ethion, ethylenethiourea, ETU, fenoxycarb, fentrothion, fenvalerate, fipronil, fosetyl-aluminium, gamma-cyhalothrin, glufosinate-ammonium, glyphosate, hexaconazole, kasugamycine, lambda-cyhalothrin, lindano, malathion, maleic hydrazide, mancozeb, mepiquat, methamidophos, methornyl, methyl bromide, N-acetyl-AMPA, N-acetyl-glufosinate, N-acetyl-glyphosate, nicotine, paraquat, parathion, parathion-methyl, perchlorate, permethrin, phosphonic acid, profenofos, propylenethiourea, PTU, TCP, terbufos, thyametoxan, trifurin, trimesium and combinations thereof. In some embodiments, the polar pesticide(s) can be selected from the group consisting of ethephon, 2-hydroxyethyl phosphonic acid (HEPA), glufosinate-ammonium, N-acetyl-glufosinate, 3-methylphosphinicopropionic acid (MPPA), glyphosate, aminomethylphosphonic acid (AMPA), N-acetyl-glyphosate, N-acetyl-AMPA, fosetyl-aluminium, phosphonic acid, maleic hydrazide, perchlorate, chlorate, cyromazine, amitrole, daminozide, ethylenethiourea, propylenethiourea, chlormequat, mepiquat, diquat, paraquat, and metabolites thereof, and combinations thereof.

In another embodiment, the list of applicable polar pesticides can include ethephon, glufosinate-ammonium, glyphosate, fosetyl-aluminium, phosphonic acid, maleic hydrazide, perchlorate, chlorate, cyromazine, amitrole, daminozide, ethylenethiourea, propylenethiourea, chlormequat, mepiquat, diquat, paraquat, and metabolites thereof, and combinations thereof.

For samples containing at least two polar pesticides, at least two or more of the pesticides can be isobaric compounds. In one embodiment, any isobaric polar pesticides in the sample can be substantially resolved, e.g., have a resolution greater than about 1. The sample can contain two or more groups of isobaric compounds. In one embodiment, the sample can contain both AMPA and fosetyl-aluminum. In other embodiments, the present methodology can be extended to other polar compounds, such as those related to veterinary medicines, marine biotoxins and metabolomics.

The methodology of the present disclosure can determine the amount of the at least one polar pesticide measured in the sample at levels which satisfy regulatory and industry requirements. The sample, or extracted sample or concentrated sample, can contain or can be determined to contain about, more than about, or less than about, 0.1 ppb, 0.5, 1, 5, 10, 50, 100, 250, 500, 750, 1000, 5000, 10000, 50000, 75000 and about 100000 ppb of each polar pesticide. These values can define a range for each pesticide, such as from about 0.5 to about 100000 ppb, or from about 0.5 to about 500 ppm, or from about 5 to about 250 ppb.

Figure 2:
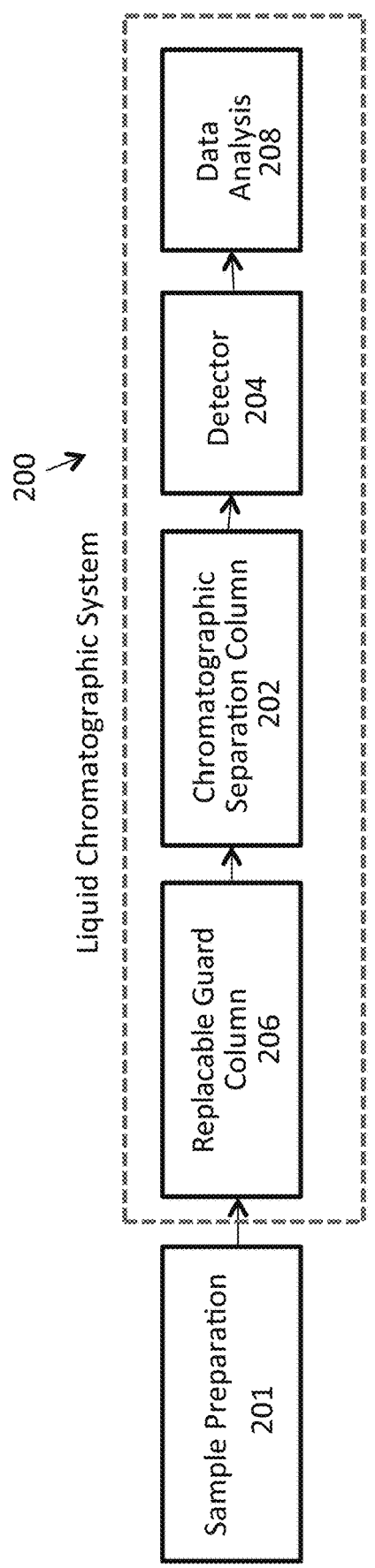
FIG. 2 is a schematic of a liquid chromatographic system, according to an illustrative embodiment of the technology.
Figure 3D:
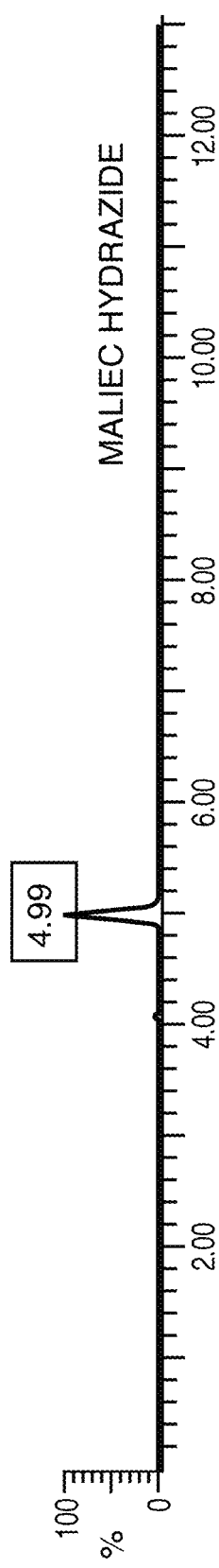
Figure 3E:
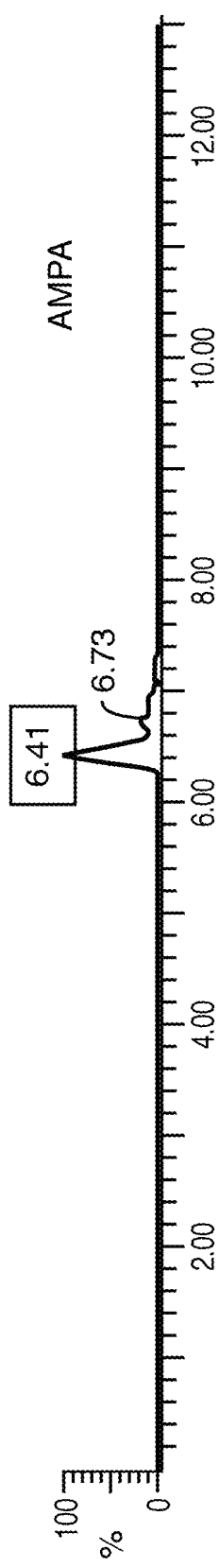
Figure 3F:
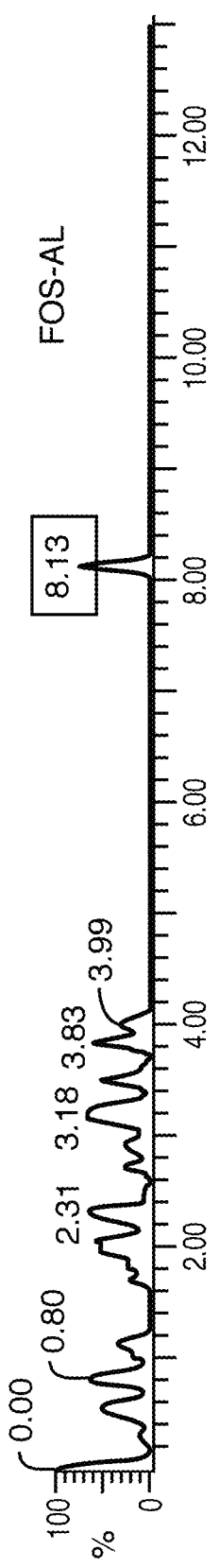
Figure 3G:
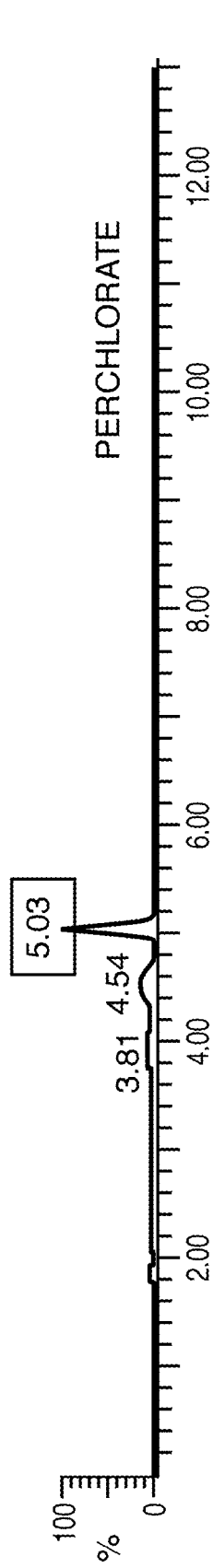
Figure 3H:
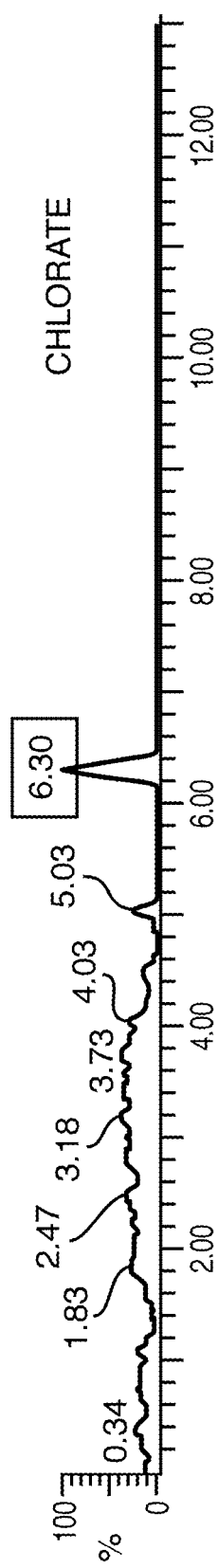
Figure 3I:
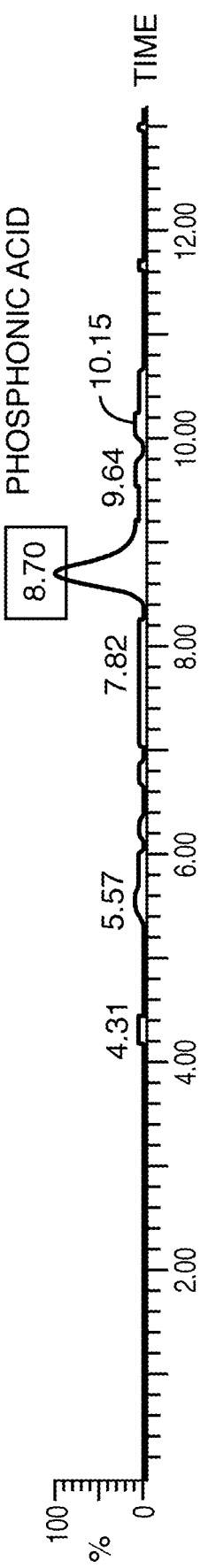
Figure 4A:
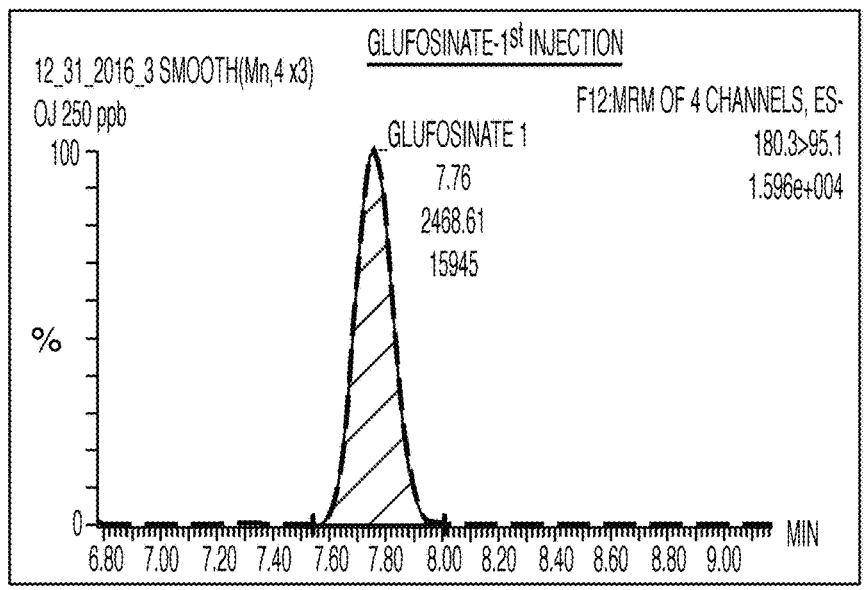
FIGS. 4A-4I are chromatograms showing how peak shape of glufosinate (FIGS. 4A-4C), glyphosate (FIGS. 4D-4F), and AMPA (FIGS. 4G-4I) can be affected during large batches of matrix injections, according to an illustrative embodiment of the technology.
Figure 4B:
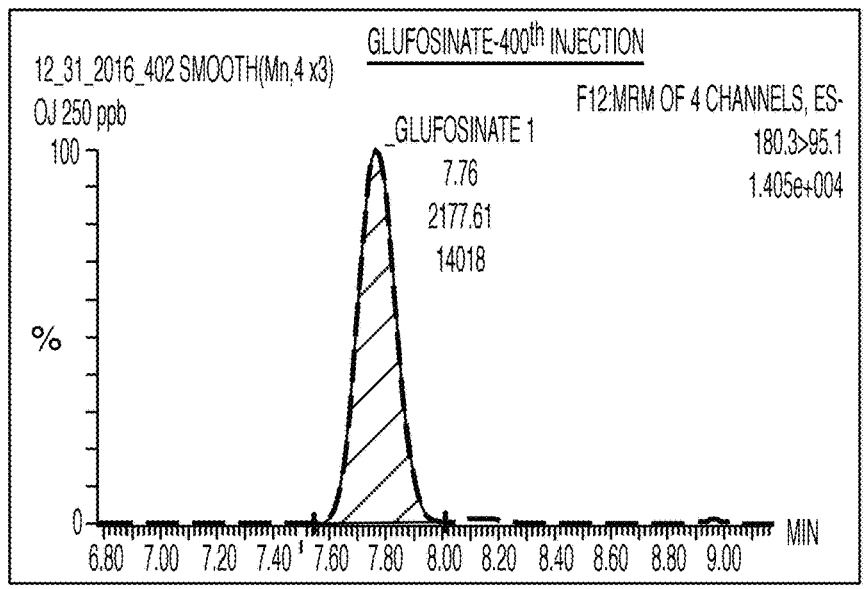
Figure 4C:
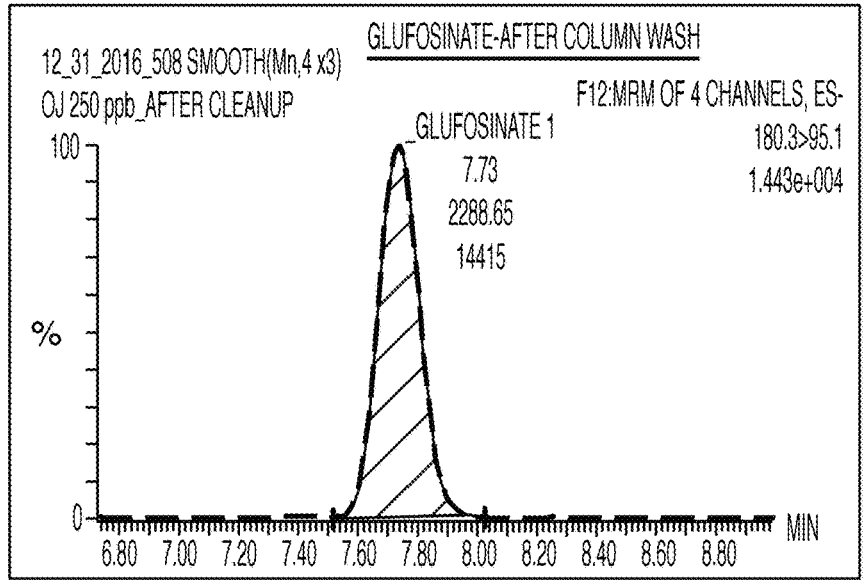
Figure 4D:
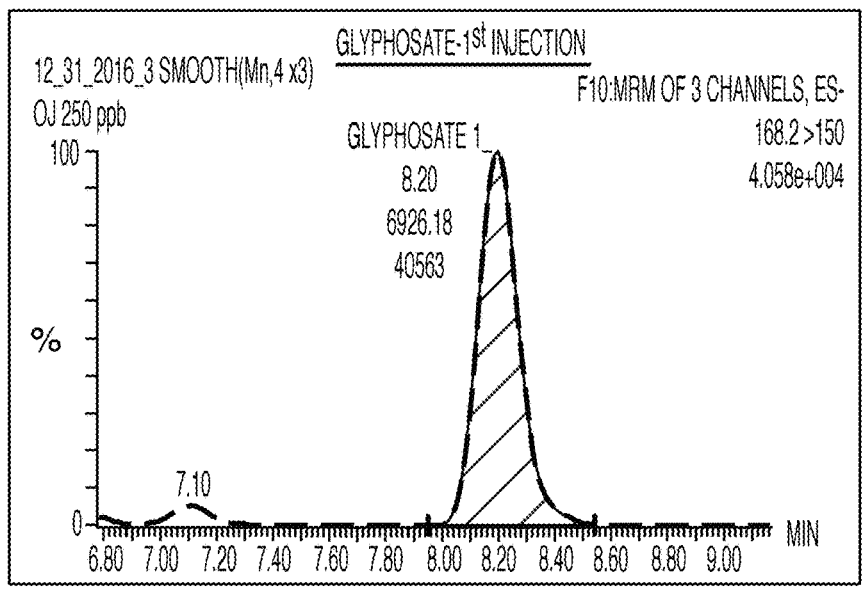
Figure 4E:
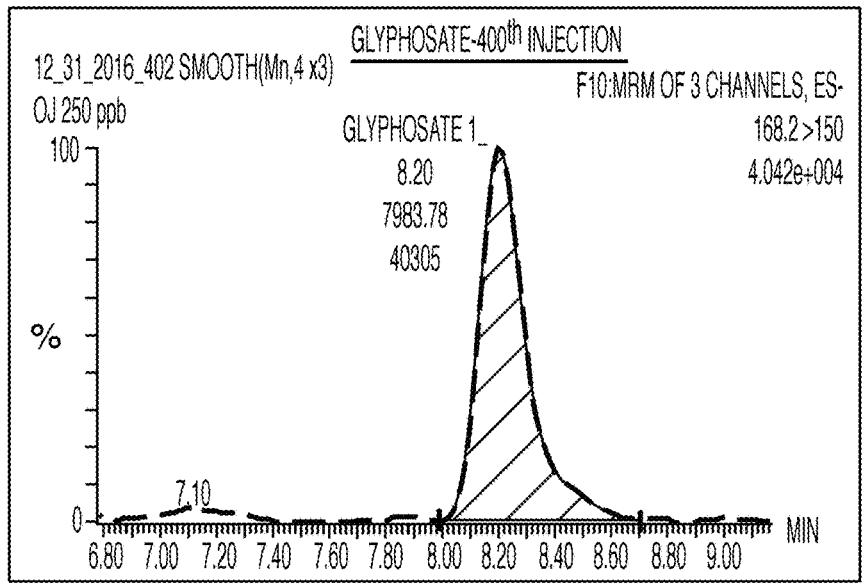
Figure 4F:
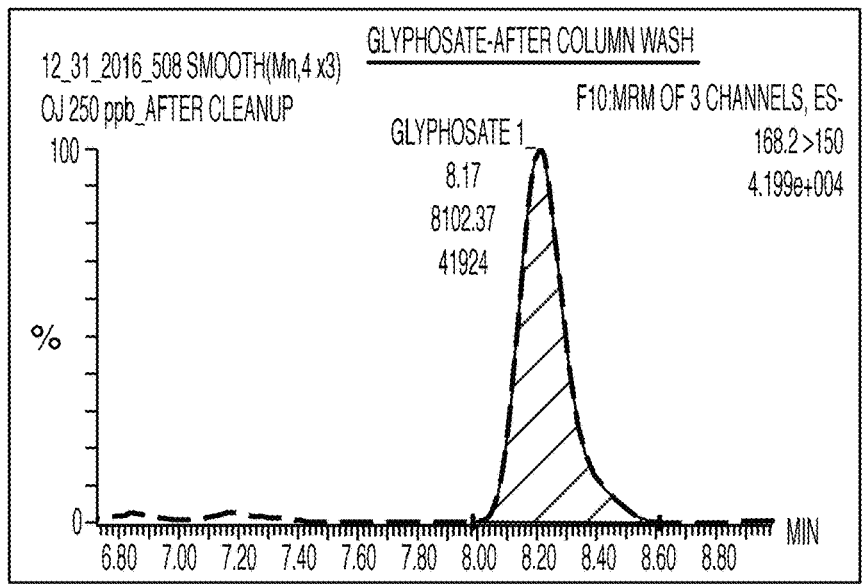
Figure 4G:
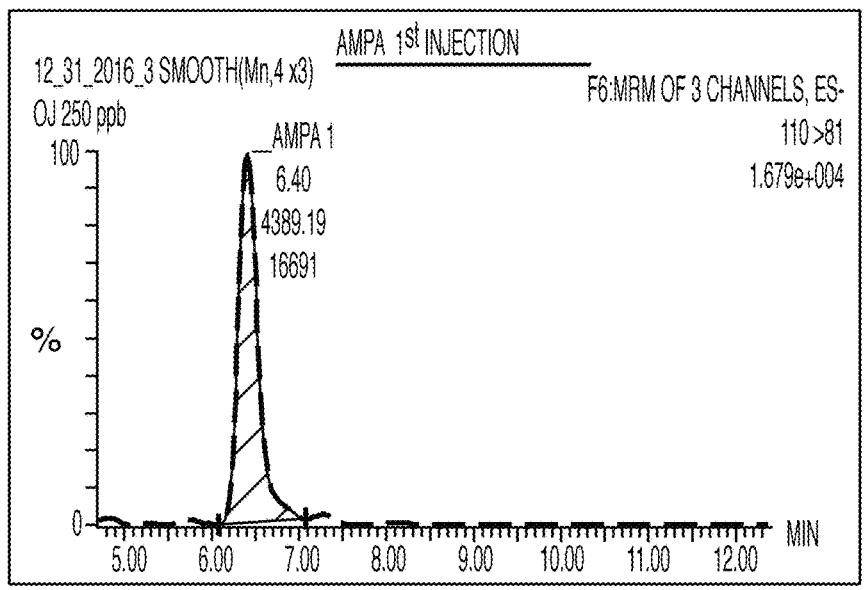
Figure 4H:
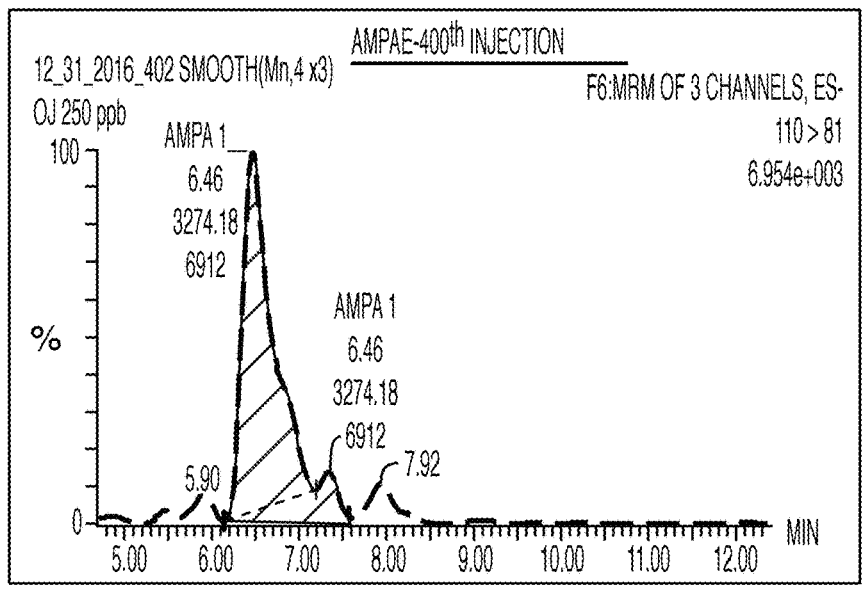
Figure 4I:
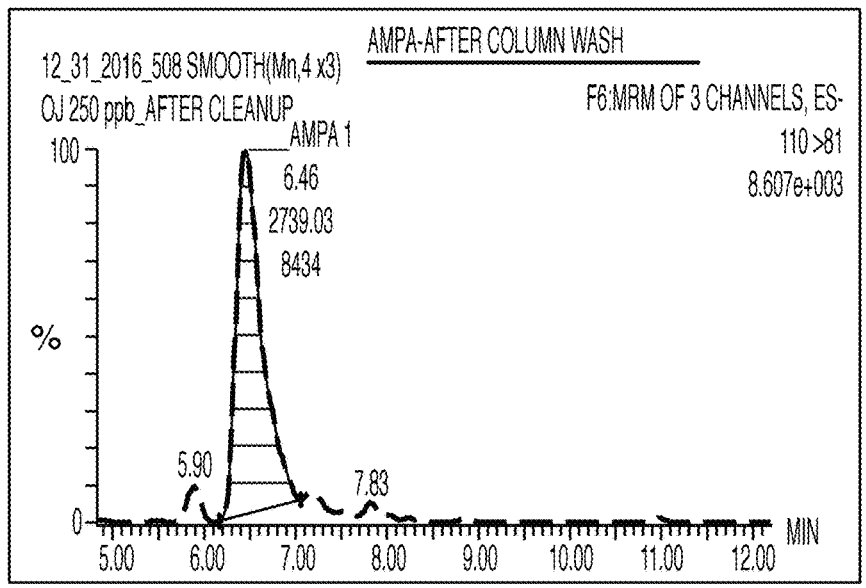
Figure 5A:
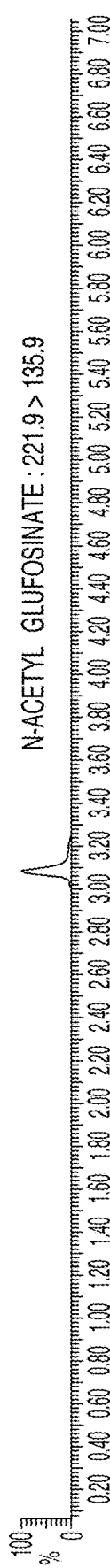
FIG. 5A-5M are chromatograms showing an example of chromatographic performance at 0.05 mg/L for n-acetyl glufosinate (FIG. 5A), n-acetyl glyphosate (FIG. 5B), glyphosate (FIG. 5C), glufosinate (FIG. 5D), MPPA (FIG. 5E), ethephon (FIG. 5F), ethephon hydroxyl (FIG. 5G), maleic hydrazide (FIG. 5H), fosetyl (FIG. 5I), AMPA (FIG. 5J), perchlorate (FIG. 5K), chlorate (FIG. 5L), and phosphonic acid (FIG. 5M) in extraction solvent, according to an illustrative embodiment of the technology.
Figure 5B:
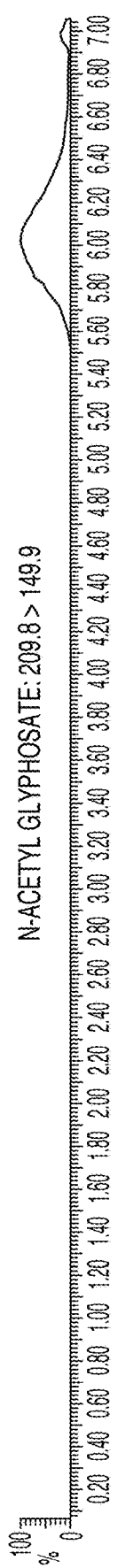
Figure 5C:
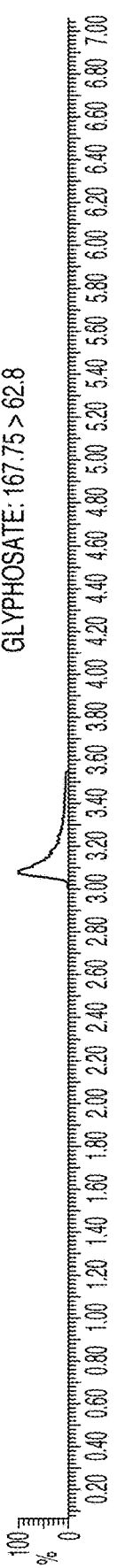
Figure 5D:
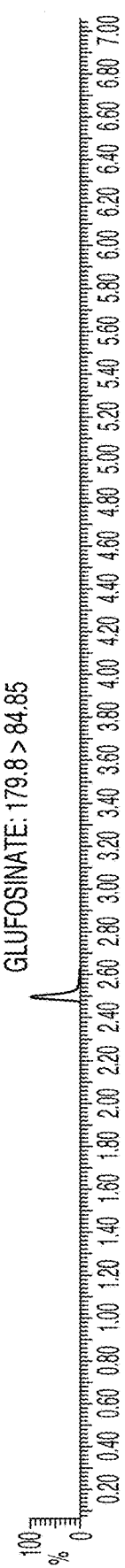
Figure 5E:
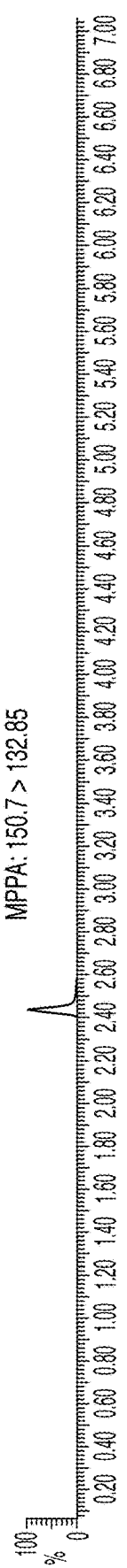
Figure 5F:
Figure 5G:
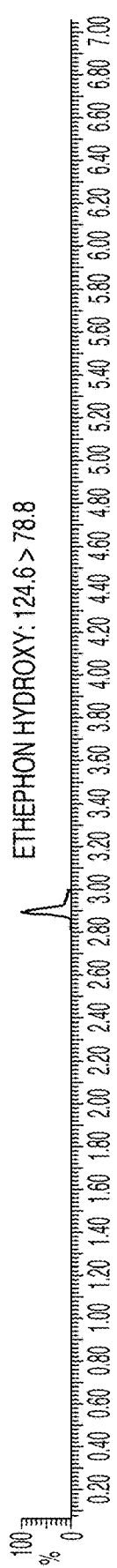
Figure 5H:
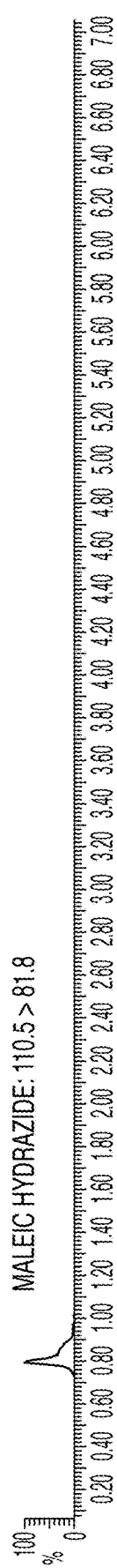
Figure 5I:
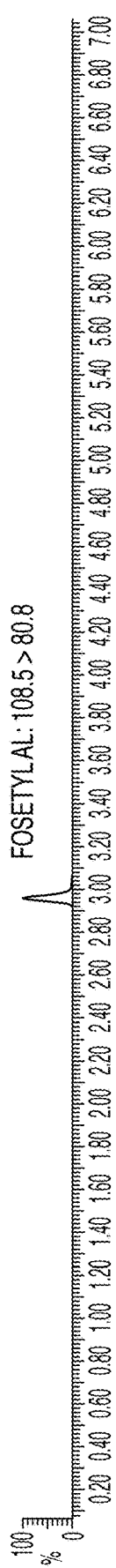
Figure 5J:
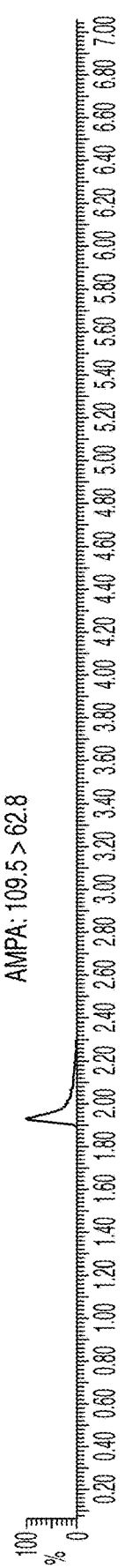
Figure 5K:
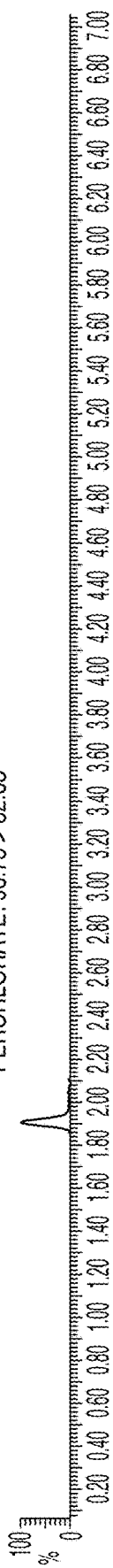
Figure 5L:
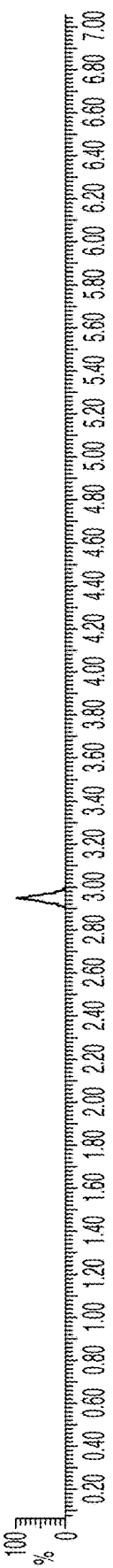
Figure 5M:
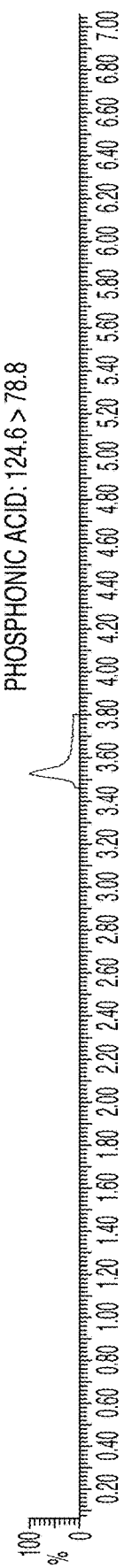

FIG. 2 shows a liquid chromatographic system 200. After the sample is prepared 201, the sample enters the chromatography system 200. Any chromatography system 200 that is capable of obtaining, retaining, separating and detecting the polar pesticide(s) in a sample matrix using a robust method can be used. The chromatography system 200 can have an autosampler (not shown), pump(s) (not shown), injector (not shown), column 202 and detector 204. The system 200 can include different liquid chromatography systems, including I-class, H-class, M-class, H-class bio, etc. For example, the chromatography system can be an ALLIANCE® HPLC system, ACQUITY® LC, ACQUITY ARC®, ACQUITY® I-Class, ACQUITY® H-Class, ACQUITY® M-Class, ACQUITY® H-Class Bio, ACQUITY UPC$^2$®, ACQUITY ULTRA PERFORMANCE LC®, all commercially available from Waters Corporation, Milford, Mass., USA.

The chromatography column can have any inner diameter that allows for the efficient separation of polar pesticides in the chromatography system as disclosed. The inner diameter can be about, more than about, or less than about, 0.05 mm, 0.075, 0.1, 0.2, 0.3, 0.4, 0.5, 0.6, 0.7, 0.8, 0.9, 1.0, 2, 2.1, 3.0, 4, 4.6, 5, 6, 7, 7.8, 8, 9, 10, 11, 12, 13, 14 or about 15 mm. These values can be used to define a range, such as from about 0.075 to about 10 mm, from about 0.3 to about 7.8 mm, from about 1 to about 5 mm and from about 2 to about 3 mm. In some embodiments, the inner diameter is 2.1 mm.

Similarly, the chromatography column can have any length that allows for the efficient separation of polar pesticides in the chromatography system as disclosed. The length can be about, more than about, or less than about, 5 mm, 20, 50, 75, 100, 150, 200, 250 or about 300 mm. These values can be used to define a range, such as from about 50 to about 150 mm. The column length can be inclusive or exclusive of a guard column having the same or similar chemistry.

The present apparatus and methodology can be configured to cope with or accommodate high pressure/backpressure generated at typical UPLC flow rates. The apparatus can tolerate the high pressures, in part, due to the stationary phase material having inorganic/organic hybrid particles. These particles can include ethylene-bridges, e.g., ethylene-bridged particles. The stationary phase material can operate under a pressure at or above 1000 psi, 2000, 3000, 4000, 5000, 6000, 7000, 8000, 9000, 10000, 15000, 20000, 25000, 30000, 35000 or 40000 psi. These values can be used to define a range, such as from about 2000 to about 10000 psi. U.S. Pat. Nos. 4,017,528; 6,528,167; 6,686,035; 7,175,913 and 7,919,177, which each are incorporated herein by reference in its entirety, also disclose organic-inorganic hybrid materials and ethylene-bridged (BEH) particles.

The chromatography column can include a stationary phase material that has a mean pore volume that allows for the efficient separation of polar pesticides in the chromatography system as disclosed. The mean pore volume can be about, more than about, or less than about, 0.01 cm$^3$/g, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.35, 0.4, 0.45, 0.5, 0.55, 0.6, 0.75, 0.8, 0.85, 0.9, 1, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.1, 2.2, 2.3, 2.4, 2.5, 2.6, 2.7, 2.8, 2.9, 3, 3.5, 4, 4.5, or about 5 cm$^3$/g. These values can be used to define a range, such as from about 0.1 to about 2.0 cm$^3$/g, or from about 0.3 to about 1.2 cm$^3$/g, or from about 0.6 to about 1.0 cm$^3$/g The chromatography column can include a stationary phase material that has a mean pore diameter that allows for the efficient separation of polar pesticides in the chromatography system as disclosed. The mean pore diameter can be about, more than about, or less than about, 10 Angstroms (Å), 20, 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 850, 900, 950, 1000, 1050, 2000, 2050 or about 3000 Å. These values can be used to define a range, such as from about 60 to about 1000 Å, or from about 80 to about 500 Å, or from about 90 to about 150 Å.

The chromatography column can include a stationary phase material that has a surface area that allows for the efficient separation of polar pesticides in the chromatography system as disclosed. The surface area can measure about, more than about, or less than about, 10 m$^2$/g, 20, 30, 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, or 700 m$^2$/g. These values can be used to define a range, such as from about 80 to about 400 m$^2$/g, or from about 100 to about 200 m$^2$/g.

The chromatography column can include a stationary phase material comprising particles having a mean size that allows for the efficient separation of polar pesticides in the chromatography system as disclosed. The mean particle size can measure about, more than about, or less than about, 0.1 µm, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 µm. These values can be used to define a range, such as from about 1 to about 10 µm, or from about 1.5 to about 5 µm, or from about 1.6 to about 2.7 µm. In one embodiment, the particle size is 1.7 µm.

The stationary phase material can be configured to retain and separate polar pesticides. The stationary phase material can include an amine functional group. The amine functional group can include diethyl amine, 2-picolylamine, 2-ethylpyridine, 4-ethylpyridine or combinations thereof. The stationary phase can also include divynylbenzene (DVB) and N-vinylpyrrolidone (NVP) functionalized a quarternary amine or an alkyl-quarternary amine, such as an Oasis Max®, commercially available from Waters Corporation, Milford, Mass., USA. The amine functional group concentration can be about, more than about, or less than about 0.1 µmol/m$^2$, 0.15, 0.2, 0.25, 0.3, 0.35 0.4, 0.45, 0.5, 0.55, 0.6, 0.65, 0.7, 0.75, 0.8, 0.85, 0.9, 0.95 1, 1.1, 1.2, 1.3, 1.4, 1.5, 1.6, 1.7, 1.8, 1.9, 2, 2.2, 2.4, 2.6, 2.8, 3, 3.5, 4, 4.5, 5, 5.5, 6, 6.5, 7, 7.5 or about 8 µmol/m$^2$. These values can be used to define a range, such as from about 0.1 to about 4.0 µmol/m$^2$, or from about 0.25 to about 3.0 µmol/m$^2$, or from about 0.5 to about 2.0 µmol/m$^2$, or from about 1.0 to about 1.6 µmol/m$^2$.

The stationary phase material can also include a diol functional group. The diol functional group concentration can be about, more than about, or less than about, 0.1 µmol/m$^2$, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7, 7.5 or about 8 µmol/m$^2$. These values can be used to define a range, such as from about 3.5 to about 5.5 µmol/m$^2$, or from about 4 to about 5 µmol/m$^2$. The ratio of amine functional group to diol functional group can also be about 0.01:1, 0.02:1, 0.03:1, 0.04:1, 0.05:1, 0.06:1, 0.07:1, 0.08:1, 0.09:1, 0.1:1, 0.2:1, 0.3:1, 0.4:1, 0.5:1, 0.6:1, 0.7:1, 0.8:1, 0.9:1 or about 1:1. These values can also be used to define a range, such as about 0.1:1 to 1:1.

U.S. 2014/0319057, U.S. 2015/0133294; U.S. 2015/0136700; U.S. 2016/0184736 and WO2016176461, which are each incorporated herein by reference in its entirety, also disclose columns, supports and stationary phase coatings and their characteristics and performance.

Referring back to FIG. 2, the apparatus and methodology can also use a guard column 206 upstream of the column 202. The guard column 206 can have the same packing material as the column 202, can have different packing material as the column 202, can have a C18 bonded phase, can have a different packing material size, or combinations thereof.

In one embodiment, the present disclosure relates to the direct analysis of anionic polar pesticides using a column having ethylene-bridged (BEH) hybrid stationary phase particles, such as a Torus® DEA column, commercially available from Waters Corporation, Milford, Mass., USA.

The mobile phase eluent (or mobile phase) and a mobile phase gradient can be used and configured to retain, separate and elute polar pesticides. The mobile phase can include organic and aqueous solvents with buffer. In one embodiment, the mobile phase can include acetonitrile, aqueous buffer or combinations thereof. The mobile phase can include, for example, mobile phase A (50 mM ammonium formate, pH 2.9) and mobile phase B (acetonitrile). The mobile phase can include, for example, mobile phase A (50 mM ammonium formate pH 2.9) and mobile phase B (acetonitrile and 0.9% formic acid). The chromatography system can include a mobile phase having a flow rate that allows for the efficient separation of polar pesticides in the chromatography system as disclosed. The mobile phase flow rate can be about, more than about, or less than about 0.01 mL/min, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.35, 0.4, 0.45, 0.5, 0.55, 0.6, 0.65, 0.7, 0.75, 0.8, 0.85, 0.9, 1, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.1, 2.2, 2.3, 2.4, 2.5, 2.6, 2.7, 2.8, 2.9, 3, 3.5, or 4 mL/min. These values can be used to define a range, such as from about 0.2 to about 1.0, or from about 1.0 to about 1.5 mL/min. These ranges can be associated with specific column inner diameters, such as for up to about 4.6 mm. The flow rate can be scaled appropriately based on column diameter and particle size.

The methodology can include a mobile phase including organic and aqueous solvents containing buffer, and wherein the polar pesticide(s) to be determined can be eluted using a gradient elution. In one embodiment using a two solvent system, the elution can include a gradient of a first solvent comprising an aqueous solvent and a second solvent comprising an organic solvent. As one skilled in the art would understand, similar gradients using multiple solvent can also be used. An exemplary gradient is provided in Table 1.

TABLE 1

Exemplary Gradient Conditions

| Time (Min) | First Solvent (%) | Second Solvent (%) |
|---|---|---|
| 0 | 1 | 100 |
| 1-3 | 0 | 100 |
| 4-6 | 30-50 | 50-70 |
| 7-9 | 100 | 0 |
| 11-13 | 100 | 0 |
| 11.1-13.1 | 0 | 100 |
| 18-22 | 0 | 100 |

The column temperature can also be configured to retain and separate polar pesticides. The column temperature can be about, more than about, or less than about, 1° C., 5, 10, 15, 20, 25, 30, 35, 40, 45, 50, 60, 70, 80, 90, 100, 120, 140, 160, 180, or about 200° C. These values can be used to define a range, such as from about 30 to about 60° C., or from about 20 to about 40° C.

The buffer contained in the mobile phase can include formate, acetate, carbonate or combinations thereof. The concentration of buffer can be about, more than about, or less than about 1 mM, 2, 3, 4, 5, 6, 7, 8, 9, 10, 20, 30, 40, 50, 60, 70, 80, 90, 100, 120, 140, 160, 180, 200, 250, 300, 350, 400, 450, 500, 550, 600, 650, 700, 750, 800, 850, 900, 950 or 1000 mM buffer. These values can be used to define a range, such as from about 10 to about 400 mM, or from about 50 to about 100 mM.

The chromatography column can include a mobile phase with a pH that allows for the efficient separation of polar pesticides in the chromatography system as disclosed. The pH of the mobile phase can be about, more than about, or less than about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.5, 5, 5.5, 6, 6.5, 7, 7.5, 8, 8.5, 9, 9.5, 10, 10.5, 11, 11.5, 12, 12.5, 13, 13.5, or about 14 pH units. These values can be used to define a range, such as from about 1 to about 7 pH units, or from about 2 to about 2.9 pH units.

The apparatus and methodology of the present disclosure can retain and separate one or more polar pesticides. The retention of the polar pesticides is improved compared to the prior art for the one or more polar pesticides. The retention time for one or more of the polar pesticides determined by the methodology can be at least about 1.5 times the retention time corresponding to the void volume of the column. In other embodiments, the retention time can be about, or more than about 1.5×, 2, 2.5, 3, 3.5, 4, 4.5 or about 5.0× the retention time corresponding to the void volume of the column. These values can be used to define a range, such as from about 2 to about 3×, or from about 3 to about 4×. The absolute retention time of one or more of the polar pesticides can be about, or longer than about, 0.5 min, 1, 1.5, 2, 2.5, 3, 3.5, 4, 4.5, 5, 5.5, 6, 6.5, 7, 7.5, 8, 8.5, 9, 9.5 or about 10 minutes. These values can be used to define a range, such as about 5 to about 10 minutes.

The apparatus and methodology of the present disclosure for the separation of polar pesticides is robust and repeatable. In one embodiment, the method repeatability of performing the methodology of the present disclosure at least 10 times using the same chromatography system and measuring peak retention time has an RSD of about, or less than about, 0.2%, 0.5, 1, 1.5, 2, 2.5, 3, 3.5, 4, 4.5 or about 5%. The sample can be a solution of one or more polar pesticide reference standards. These values can be used to define a range, such as about 0.5 to about 3%. The methodology of the present disclosure can be repeated about, or more than about 10 times, 20, 30, 40, 50, 60, 70, 80, 90, 100, 120, 140, 160, 180, 200, 250, 300, 350, 400, 450, 500, 550, 600, 650, 700, 750, 800, 850, 900, 950, 1000, 1500, 2000, 2500, 3000, 3500, 4000, 4500 or about 5000 times. These values can be used to define a range, such as from about 10 to about 2000 times, from about 10 to about 1000 times, from about 50 to about 500 times, or from about 200 to about 400 times. The repeatability can also occur with about or less than about 10%, 9, 8, 7, 6, 5, 4, 3, 2 or about 1% increase in backpressure. These values can be used to define a range, such as from about 1% to about 5%. In some embodiments, there can be no observable increase in backpressure.

The apparatus and methodology of the present disclosure can separate and resolve one or more polar pesticide. The substantially resolved polar pesticides, at least one or more pairs of peaks, can have a resolution about, or greater than about, 1, 1.1, 1.2, 1.3, 1.4, 1.5, 1.6, 1.7, 1.8, 1.9 or about 2. In some embodiments, at least one critical pair of polar pesticides can be identified in a sample and the pair(s) can be substantially resolved. The linearity of the methodology, or fit of the line, can also be defined. The fit of the line applied to a calibration graph for one or more of the polar pesticides measured has a correlation coefficient value can be about, or greater than about, 0.9, over at least 1 order of magnitude in concentration, or over at least 2 orders of magnitude in concentration. The correlation coefficient can also be about, or greater than about, 0.95, 0.96, 0.97, 0.98, 0.99, 0.999, 0.9999, or about 0.99999, and can be over 1, 2, 3, 4, or 5 orders of magnitude, or any combination thereof. These values can be used to define a range, such as from about 0.98 to about 0.999 over from 2 to 4 orders of magnitude.

Referring back to FIG. 2, the chromatography system detector 204 can be any detector useful for determining polar pesticides. The detector 204 can be used to qualitatively determine, quantitatively determine or both, the polar pesticides, Data analysis 208 can be done by computers or equipment connected to the detector 204. The detector 204 can be selected from the group consisting of a UV/VIS detector, PDA detector, fluorescence detector, mass spectrometer, refractive index detector, evaporative light scattering detector and a charged aerosol detection. Various mass spectrometers can be used. For example, the mass spectrometer can be selected from the group consisting of a single quadrupole, tandem or triple quadrupole, QTOF, QTrap, Orbitrap and linear trap. In some embodiments, the mass spectrometer can be an ACQUITY QDa®, ACQUITY® SQ Detector, ACQUITY® TQ Detector, SQ Detector 2™, Xevo® TQD, Xevo® TQ-S micro, Xevo® TQ-S, Xevo® TQ-XS, Xevo® G2-XS TOF, Xevo® G2-XS QTOF, SYNAPT® G2-Si MS, MALDI SYNAPT® G2-Si MS, Vion® IMS QTOF, SYNAPT® G2-Si HDMS, MALDI SYNAPT® G2-Si HDMS, all commercially available from Waters Corporation, Milford, Mass., USA. The mass spectrometer can be a quadrupole fitted with an interface for integrated operations with multiple devices. The mass spectrometer can also be configured to for scanning (mass to charge scan), SIR (selected ion recording), MRM (multiple reaction monitoring), MSe (high and low fragmentation energy) and/or combinations thereof, e.g., radar (both scanning and SIR together or full scan and MRM run simultaneously), such as with the ACQUITY QDa®, commercially available from Waters Corporation, Milford, Mass., USA.

In some embodiments, the methodology of the present disclosure can be performed without the added requirements of other methods, such as without extractions, derivatization, ion pair reagents, or special equipment. For example, the method can exclude an extraction step, a derivatization step, the use of special equipment, such as an ion chromatography system with chemical or membrane suppressor, or combinations thereof.

The present disclosure also relates to a kit. The kit can include a chromatography system, as described herein, including a column and a detector. The column can have a stationary phase material contained inside. The kit can also have instructions for obtaining a sample containing at least one polar pesticide in a sample matrix. The kit can also have instructions for introducing the sample to the chromatography system. The kit can also have instructions for flowing the sample with a mobile phase eluent through the column, wherein the at least one polar pesticide is substantially resolved, retained, or both. The kit can also have instructions for detecting the resolved and retained at least one polar pesticide using a detector.

In some embodiments, the kit can further including instructions for extracting an extraction sample from the sample matrix, as provided herein. Similarly, the kit can also include instructions for excluding an extraction step, a derivatization step, ion pair reagents, the use of special equipment, such as an ion chromatography system with chemical or membrane suppressor, ion pair reagents, or combinations thereof.

The methodology can include the use of polar pesticide standards. The kit can include the polar pesticide standards. The standards can be used to create a single point calibration, one or more threshold calibrators to determine if a sample has less than or greater than the standard(s) amounts, or a multipoint calibration curve. One or more of the polar pesticide standards can be an isotopically labeled standard. The methodology can employ a first known quantity of a first calibrator and a second known quantity of a second calibrator (as well as additional calibrators up to and including a sixth known quantity of a sixth calibrator, etc.) where the first known quantity and the second known quantity are different, and the first calibrator, the second calibrator, and the target polar pesticide are each distinguishable in the sample by mass spectrometry, to quantify the target polar pesticide in the sample. The calibrators and/or the target polar pesticide can be distinguishable, for example, on the basis of isotopic substitution and/or chemical function group substitution. U.S. 20140158881, which is incorporated herein by reference in its entirety, also discloses isotopically labeled standards and their use to determine a target analyte (e.g., polar pesticide). Finally, the methodology and kit can further use and include spiked standards in the sample matrix or a substantially equivalent sample matrix.

In one embodiment, the kit can include standards and/or isotopically labeled standards. The kit can be a proficiency test kit. The kit can also include instructions for downloading a report template for the methodology.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Polar pesticides in orange juice were determined using the methodology of the present disclosure. The following polar pesticides were tested: glyphosate, AMPA, glufosinate, perchlorate, ethephon, fosetyl-aluminium, maleic hydrazide, phosphonic acid and chlorate. The MS conditions for each of these polar pesticides is shown in Table 2. A sample of orange juice was extracted using the QuPPe extraction method. A 10 mL portion of sample was acidified with 10 mL of 1% formic acid in MeOH. The mixture was shaken for 10 minutes, and centrifuged for 5 minutes at 4000 rpm. The mixture was then filtered with a 0.45 micron filter. The filtered sample extract was spiked with about 250 ppb of each pesticide and then introduced to the chromatography system.

TABLE 2

Example 1 MS Conditions

| Compound | Ion Mode | Transitions | Cone Voltage (V) | Collision Energy (eV) |
|---|---|---|---|---|
| Glyphosate | ESI– | 167.70 > 63 | 30 | 16 |
| | | 167.70 > 81 | | 15 |
| | | 167.70 > 150 | | 8 |
| AMPA | ESI– | 109.5 > 63 | 30 | 15 |
| | | 109.5 > 79 | | 15 |
| | | 109.8 > 81 | | 12 |

TABLE 2-continued

Example 1 MS Conditions

| Compound | Ion Mode | Transitions | Cone Voltage (V) | Collision Energy (eV) |
|---|---|---|---|---|
| Glufosinate | ESI− | 179.8 > 62.9 | 30 | 25 |
|  |  | 179.8 > 81 |  | 16 |
|  |  | 179.8 > 134.1 |  | 16 |
|  |  | 179.8 > 95.1 |  | 16 |
| Perchlorate | ESI− | 98.5 > 83 | 25 | 15 |
|  |  | 100.4 > 84.5 |  | 15 |
| Ethephon | ESI− | 142.7 > 78.9 | 20 | 15 |
|  |  | 142.7 > 107 |  | 10 |
| Fosethyl Aluminum | ESI− | 108.5 > 63 | 20 | 15 |
|  |  | 108.5 > 80.9 |  | 10 |
| Maleic hydrazyde | ESI+ | 112.5 > 43.5 | 25 | 10 |
|  |  | 112.5 > 67 |  | 15 |
|  |  | 112.5 > 85.1 |  | 10 |
|  |  | 112.5 > 95 |  | 10 |
| Phosphonic acid | ESI− | 80.8 > 78.8 | 20 | 14 |
|  |  | 80.8 > 62.8 |  | 12 |
| Chlorate | ESI− | 82.4 > 66.8 | 25 | 15 |
|  |  | 84.4 > 68.9 |  | 15 |
| Maleic hydrazyde | ESI− | 110.6 > 55 | 20 | 15 |
|  |  | 110.6 > 82 |  | 15 |
|  |  | 110.6 > 83 |  | 10 |

The chromatography system included an ACQUITY® UPC$^2$® system commercially available from Waters Corporation, Milford, Mass., USA. The column was a TORUS® DEA column, 3×100 mm, 130 Angstroms, 1.7 micron particle, commercially available from Waters Corporation, Milford, Mass., USA. The LC system was an ACQUITY® I class (FTN). The detector was a Xevo® TQ-XS detector, commercially available from Waters Corporation, Milford, Mass., USA.

The mobile phase included solvent A: 50 mM ammonium formate, pH 2.9 and solvent B: ACN and solvent. The sample injection volume was 10 microliters. The column temperature was 40° C. The sample temperature was 10° C. The mobile phase gradient used is in Table 3:

TABLE 3

Example 1 Gradient Conditions

| Time (Min) | A (%) | B (%) |
|---|---|---|
| 0 | 0 | 100 |
| 2 | 0 | 100 |
| 5 | 40 | 60 |
| 8 | 100 | 0 |
| 12 | 100 | 0 |
| 12.1 | 0 | 100 |
| 20 | 0 | 100 |

The chromatography system proved effective for the determination of polar pesticides when coupled to existing extraction protocols. The polar pesticides demonstrated improved retention and chromatographic performance for the polar pesticides over a twenty minute runtime. Retention of all polar pesticides was greater than about 2× the void volume of the column. Two of the polar pesticides, i.e., AMPA and fosetyl-aluminium have isobaric MRM transitions, which require a chromatographic separation providing substantial resolution of these peaks. As shown in FIGS. 3A-3I, baseline separation of these compounds was achieved.

The robustness of the column was also investigated through replicate analyses of an orange juice extract, spiked with the polar pesticides. Retention time of the polar pesticides and associated peak areas were shown to be repeatable after 400 injections (RSD<0.2% and <15% respectively) with no observable increase in backpressure.

Analyses were also performed using other columns. The results of the column comparison are shown in Table 4. The apparatus and methodology of the present disclosure show a significant improvement over other columns tested, particularly in terms of repeatability; more consistent retention times than both the Acclaim and Shodex columns and better precision of response than the Acclaim, both for a much longer testing period.

TABLE 4

Column Comparison

| % RSD | Acclaim OJ @50 ug/kg | Shodex OJ @100 ug/kg | Present Disclosure OJ @250 ug/kg |
|---|---|---|---|
|  | Glyphosate | | |
| Retention time | 0.1 (n = 18) | 0.5 (n = 43) | 0.05 (n = 400) |
| Repeatability | <15 (n = 18) | 6 (n = 14) | 6.1 (n = 400) |
|  | Glufosinate | | |
| Retention time | 0.4 (n = 18) | 0.3 (n = 43) | 0.08 (n = 400) |
| Repeatability | 13.6 (n = 18) | 4.6 (n = 14) | 9.8 (n = 400) |
|  | AMPA | | |
| Retention time | 1.2 (n = 18) | 0.2 (n = 43) | 0.2 (n = 400) |
| Repeatability | <15 (n = 18) | 8.1 (n = 14) | 14.5 (n = 400) |

Example 2

Initial conditions and analytical methodology are described for the analysis of polar pesticides in extracted food matrices.

Column Equilibration: Before installing the column, the LC system can be acid washed to remove metal ions. When the column is first received, it can be flushed in 50% acetonitrile/50% (LCMS grade water) for 50 column volumes. For example, for a 3.0 mm×150 mm column, 1 column volume is equal to 1.06 mL. At the flow rate of 0.45 mL/min it takes 2.35 mins to fill one column volume. Equilibration can include 20 column volumes of initial mobile phase conditions before making a first injection.

The LC conditions can be the same as used in Example 1. An exemplary gradient is provided in Table 5.

TABLE 5

Example 2 Gradient Conditions

| Time (min) | % A | % B |
|---|---|---|
| 0 | 100 | 0 |
| 3.20 | 100 | 0 |
| 8.00 | 60 | 40 |
| 13.00 | 0 | 100 |
| 18.10 | 0 | 100 |
| 18.20 | 100 | 0 |
| 31.00 | 100 | 0 |

The LC conditions can be the same as used in Example 1. The gradient can be as provided in Table 5. The sample can include various polar pesticides including glyphosate, AMPA, glufosinate, perchlorate, ethephon, fosetyl-aluminium, maleic hydrazide, phosphonic acid and chlorate.

Referring to FIGS. 4A-4I, the peak shape of glyphosate, glufosinate and AMPA can be affected during large batches of matrix injections. This can be due to metal ion contamination in the LC system and column which can result in peak tailing. In some embodiments, a wash step can be used to ensure or recover peak shape. For example, a citric acid solution can be used to efficiently recover the initial peak shape. A washing procedure can be run after every batch run of about 100 or more samples and/or after observing unacceptable peak tailing. The procedure can include:

Washing the column with a citric acid solution (e.g., 0.5-10 mM, 5 mM) for at least about 10 or 15 minutes. The flow can be diverted to waste. Flushing the column with mobile phase B for at least about 20 or 30 minutes to wash out all remaining citric acid. The presence of citric acid can suppress signal. Re-equilibrating the column with at least about 20 or 30 column volumes of initial mobile phase conditions before making another injection. Injecting solvent standards to check peak shape and intensity. If the peak shape is still compromised, additional flushing can be attempted at a 0.2 mL/min flow rate. In some embodiments, the column can be flushed with 50:50 mobile phase A:mobile phase B.

When significant loss in sensitivity is observed, overnight washing with an organic solvent can be attempted. If loss is still observed, the inlet can be washed with an acid solution. For example, the following steps can be taken. Disconnect the MS from the LC system. Remove the column from the LC and direct the line to waste. Put solvent lines and sample manager wash in a 30% phosphoric acid in water solution. Put the purge and seal wash in the wash solution of 90:10 Water:MeOH with no additives. Do not put the seal wash line in the acid wash solution. Do not put solvent lines in acid for longer than 90 minutes. A series of injections lasting for about one hour can be performed followed by flushing with water or ordinary mobile phases to clear the acid from the system. For example, 20 injections of 3 min duration run on lines A1 B1 with acid wash. 20 injections of 3 min duration run on A2 B2 with acid wash. Cleaning of LC systems is well known and one example of cleaning an LC system can be found in the document titled "Controlling Contamination in LC/MC Systems: Best Practices" in the section titled "Cleaning to Eliminate Contamination", Waters Corporation, Milford, Mass., USA, Document Number 715001307 available at http://www.waters.com/waters-.com/webassets/cms/support/docs/715001307rg.pdf.

All solvent lines (A1 A2 B1 B2) and sample manager wash can be put in LC-MS Grade water, no additives. The following steps can be taken: Prime the system for 5 min on A2 B2, prime seal wash, prime sample manager wash (30 s and 20 cycles). Prime the system for 5 min on A1 B1, prime seal wash, prime sample manager wash (30 s and 20 cycles). Perform sufficient injections of 3 min duration run on A1 B1 to bring pH level back to water pH or to 7.0. Perform sufficient injections of 3 min duration run on A2 B2 to bring pH level back to water pH or to 7.0. Prime seal wash and sample manager wash as per the method solvents shown in section 3. An exemplary cleaning gradient is provided in Table 6.

TABLE 6

Example 2 Cleaning Gradient Conditions

| Time (min) | Flow Rate ml/min | % A | % B |
|---|---|---|---|
| 0.00 | 0.3 | 95 | 5 |
| 0.50 | 0.3 | 95 | 5 |
| 2.00 | 0.3 | 5 | 95 |
| 2.50 | 0.3 | 5 | 95 |
| 3.00 | 0.3 | 95 | 5 |

A mass spectrometer detector can be used, such as a Xevo® TQ-XS detector, commercially available from Waters Corporation, Milford, Mass., USA.

The Xevo® TQ-XS detector can be initially optimized at the conditions listed in Table 7.

TABLE 7

Example 2 MS Instrument Settings

| Parameter | Value |
|---|---|
| Ion Mode | ES negative |
| Capillary Voltage (kV) | 2.4 |
| Source temperature (C) | 150 |
| Desolvation temperature (C) | 600 |
| Cone gas flow (L/Hr) | 300 |
| Desolvation gas flow (L/Hr) | 1000 |
| Nebuliser (bar) | 7 |

These values can each be individually varied by about 1%, 2, 3, 4, 5, 6, 7, 8, 9 or 10% to optimize the detector. A relatively high cone gas flow can be used to prevent system contamination. By increasing the cone gas flow the baseline noise can be reduced significantly. A possible drawback is that relatively high concentrations of a certain compound can show a minor loss in intensity.

These initial conditions and analytical methodology can be used for the initial analysis of polar pesticides in extracted food matrices.

Example 3

Samples of onion and spinach, labelled as organic, were purchased from retail outlets, homogenized and extracted using the EURL Quick Polar Pesticides Extraction method.

TABLE 8

Example 3, Liquid Chromatography System

| | |
|---|---|
| LC System | ACQUITY UPLC I-Class |
| Column | Torus DEA 2.1 × 100 mm |
| Mobile Phase A | 50 mM ammonium formate pH 2.9 |
| Mobile Phase B | 0.9% formic acid in acetonitrile |
| Strong Wash | 10:90 acetonitrile:water |
| Weak Wash | 90:10 acetonitrile:water |
| Column Temperature | 50° C. |
| Sample Temperature | 10° C. |
| Injection volume | 10 µL |
| Flow rate | 0.5 mL/min |
| Runtime | 20 minutes |

TABLE 9

Example 3 MS Instrument Settings

| Parameter | Value |
|---|---|
| MS System | Xevo TQ-XS |
| Ionization Mode | ESI negative |
| Capillary Voltage (kV) | 2.5 |
| Source temperature (C) | 150 |
| Desolvation temperature (C) | 600 |
| Desolvation gas flow (L/hr) | 1000 |

The mobile phase gradient used is in Table 10. The gradient hold is 320 μL.

TABLE 10

Example 3 Mobile Phase Gradient

| Time (Min) | First Solvent (%) | Second Solvent (%) | Curve |
|---|---|---|---|
| 0 | 10 | 90 | |
| 4.5 | 60 | 40 | 2 |
| 8.5 | 60 | 40 | 6 |
| 20 | 10 | 90 | 1 |

The acquisition of the MS is MRM with at least 2 transitions per compound. Primary transition is reported in FIGS. 5A-5M showing an example of chromatographic performance at 0.05 mg/L for the thirteen analytes in extraction solvent.

Figure 6:
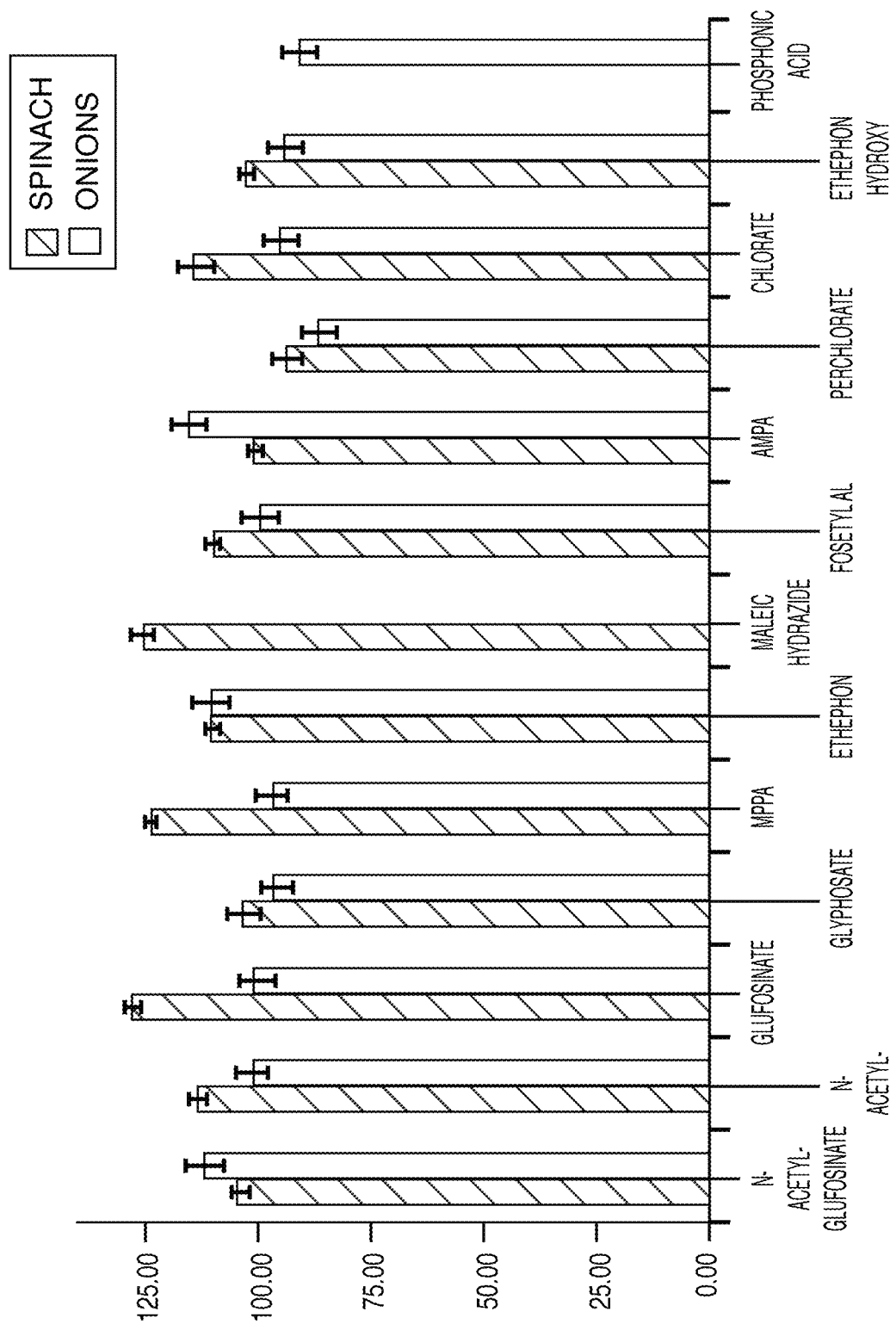
FIG. 6 is a chart showing a summary of recoveries and repeatability achieved for QuPPe extracts, spiked to 0.01 mg/kg in onion (n=5) and spinach (n=5), according to an illustrative embodiment of the technology.

Both food samples, spinach and onion were spiked to 0.01 mg/kg and extracted in accordance with the QuPPE method. Five replicates were prepared for each sample. The recoveries and repeatability achieved is summarized in FIG. 6 where excellent method performance is shown. Due to incurred residues detected in the samples, maleic hydrazide in onion and phosphonic acid in spinach, recoveries have been omitted. For the remaining 11 analytes the recoveries, which were calculated against matric matched calibration curve, fell within 80 and 125%. Repeatability, reported as % RSD was less than 20% of all 13 analytes across the two matrices. Linearity of the 13 analytes was determined in solvent and matrix matched calibration curves. Excellent performance was demonstrated in solvent, over the range of 0.0005 to 0.2 mg/L for all analytes, where residuals were <20%. Similar performance was observed in both spinach and onions matrix (residuals<22%)

However, due to the presence of incurred residues in the samples, standard addition calibration curves were generated in TargetLynx XS to reliably quantify the maleic hydrazide and phosphonic acid residues in the absence of isotopically labelled internal standard. An example is shown is FIGS. 7A and 7B, where an incurred residue of maleic hydrazide was quantified at 0.072 mg/kg in onion.

Figure 8:
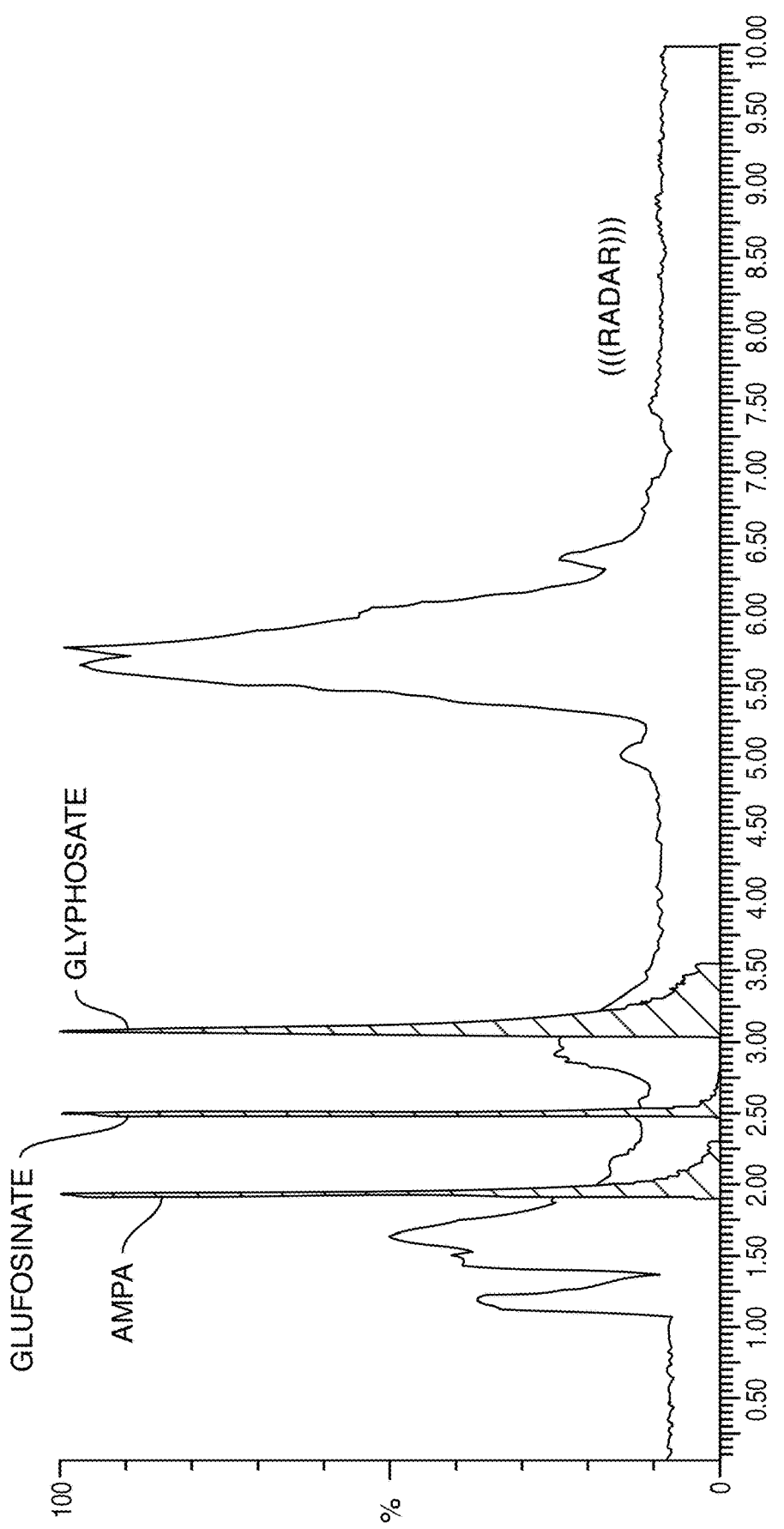
FIG. 8 is a RADAR full scan acquisition showing the complexity of matrix ionized, which can impact ionization efficiency and matrix effects of the analytes of interest, according to an illustrative embodiment of the technology.
Figure 9:
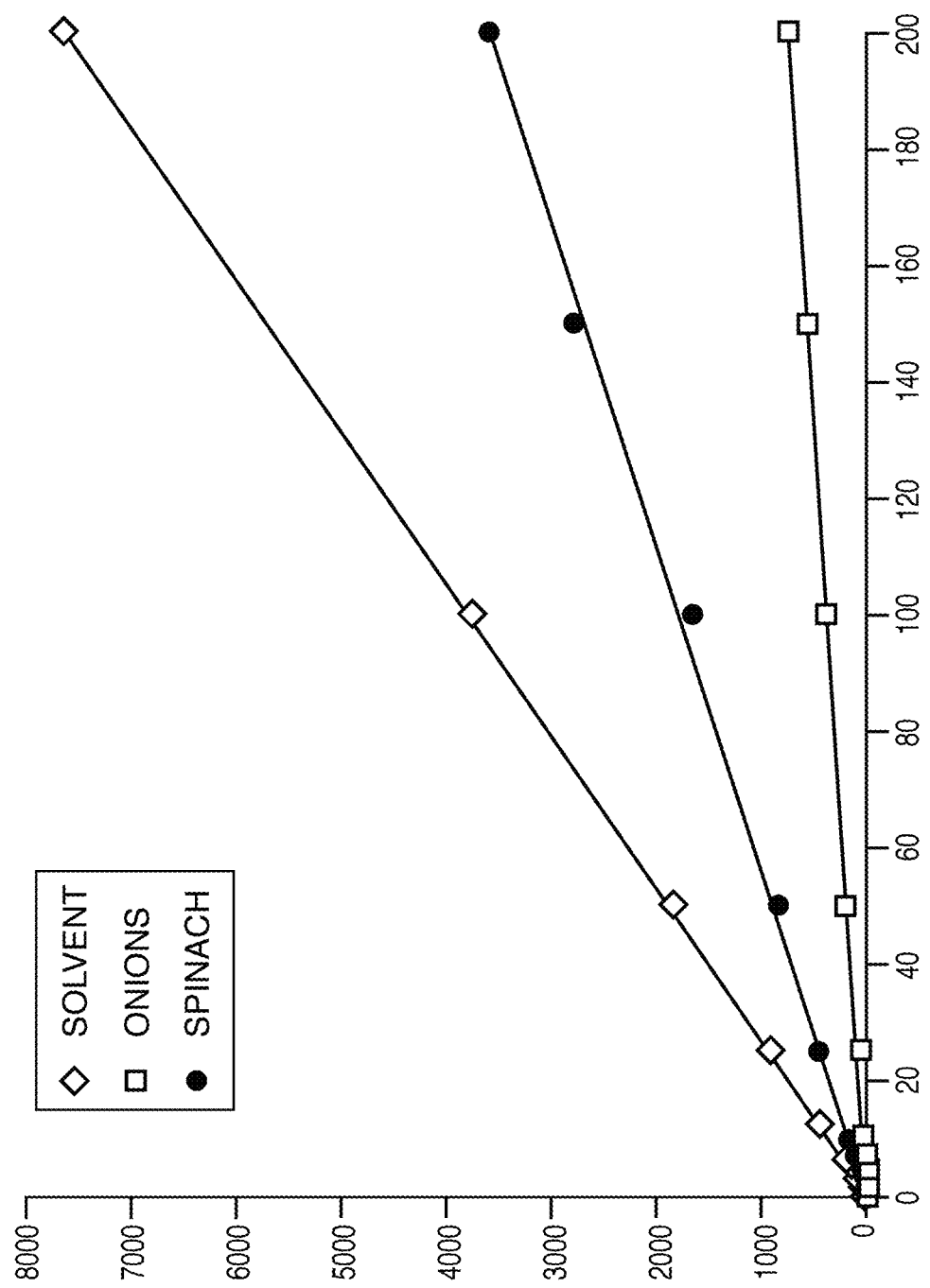
FIG. 9 is a graph showing matrix effects determined by comparing the slopes of matrix matched and solvent calibration curves, in particular, an example of AMPA curves showing significant suppression by both matrices, according to an illustrative embodiment of the technology.

All external calibration curves were also used to evaluate matrix effects, reported in FIG. 8 and FIG. 9. Comparing the slope of all curves, a value >100% signifies ion enhancement and <100% signifies suppression of ions due to matrix interferences. Aquiring a RADAR scan (full MS scan) simultaneously to the MRMs, provides additional information on matrix and background ions, as shown in FIG. 8. Table 11 summarizing enhancement (>50%) and suppression (<50%) for all analytes in onion and spinach.

TABLE 11

| | Onion (%) | Spinach (%) |
|---|---|---|
| N-Acetyl Glufosinate | 101 | 233 |
| N-Acetyl-Glyphosate | 105 | 370 |
| Glufosinate | 96 | 99 |
| Glyphosate | 109 | 104 |
| MPPA | 339 | 488 |
| Ethephon | 131 | 287 |
| Maleic hydrazide | 14 | 9 |
| Fosetyl Al | 100 | 107 |
| AMPA | 10 | 47 |
| Perchlorate | 59 | 494 |

TABLE 11-continued

| | Onion (%) | Spinach (%) |
|---|---|---|
| Chlorate | 278 | 245 |
| Ethephon hydroxyl | 131 | 156 |
| Phosphonic acid | 149 | 151 |

Figure 10:
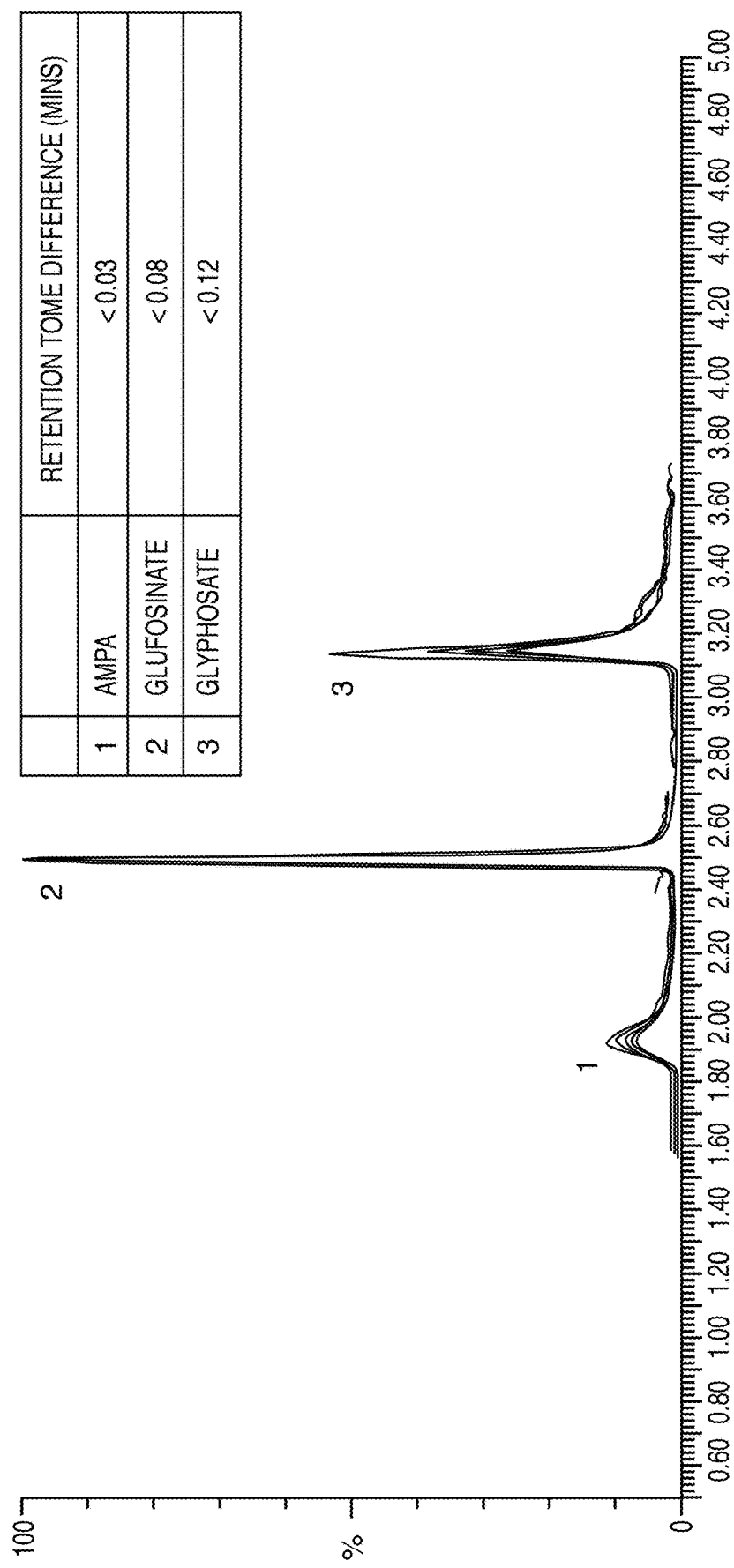
FIG. 10 is a chromatogram showing excellent interbatch repeatability (% $RSD_{retention\ time} \leq 2.2\%$ and % $RSD_{peak\ area} < 20\%$) shown for AMPA, glufosinate and glyphosate, where 0.1 mg/L standards, acquired on 6 different Torus DEA column batches are overlaid, according to an illustrative embodiment of the technology.
Figure 11A:
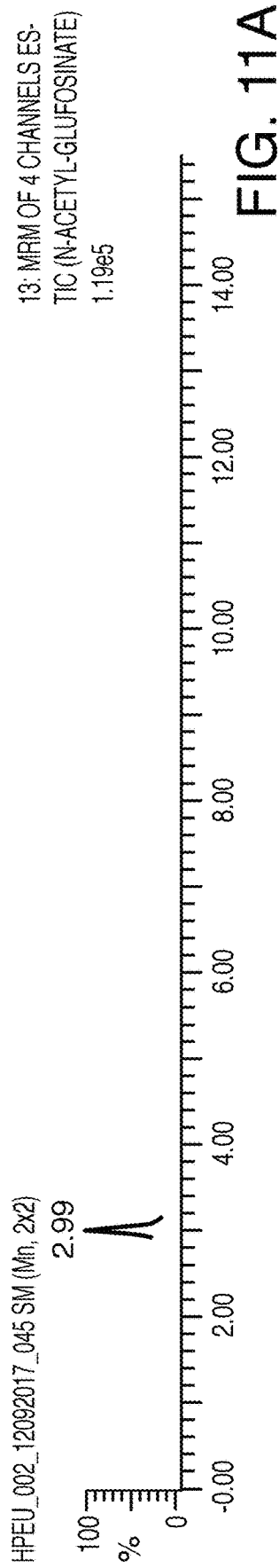
Figure 11B:
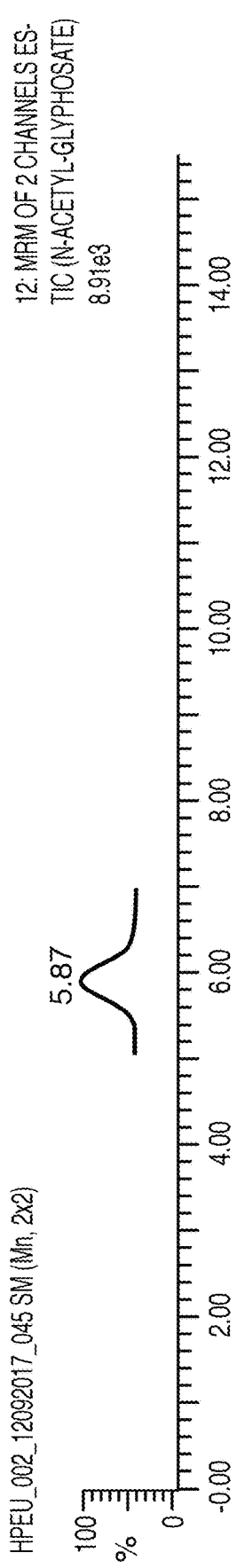
Figure 11C:
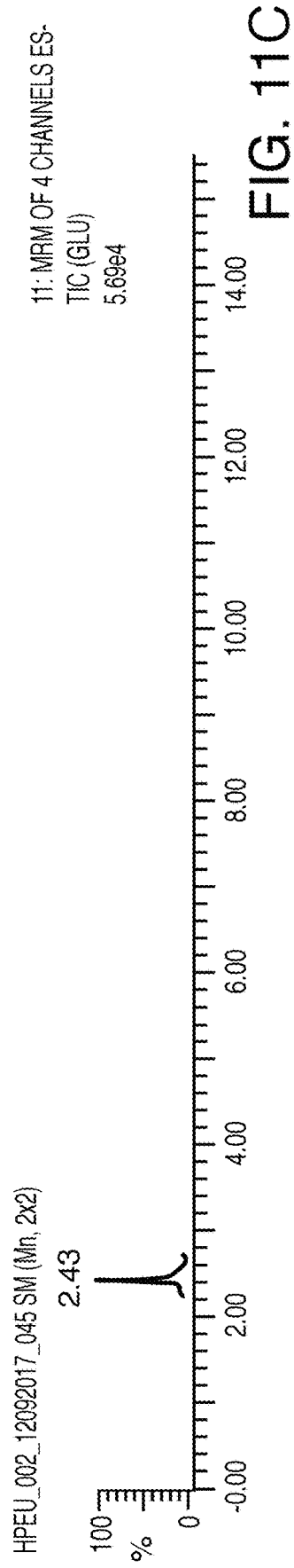
Figure 11D:
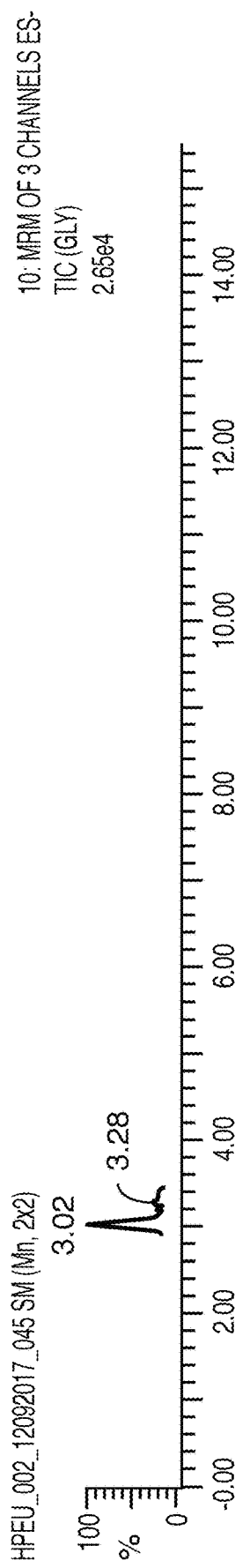
Figure 11E:
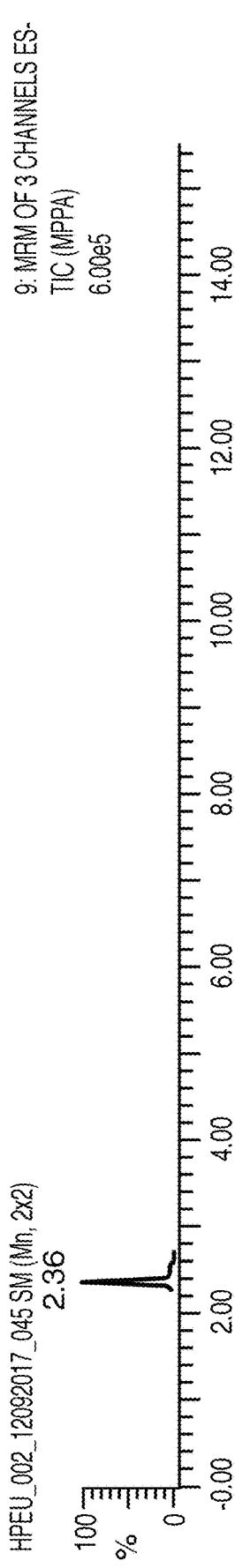
Figure 11F:
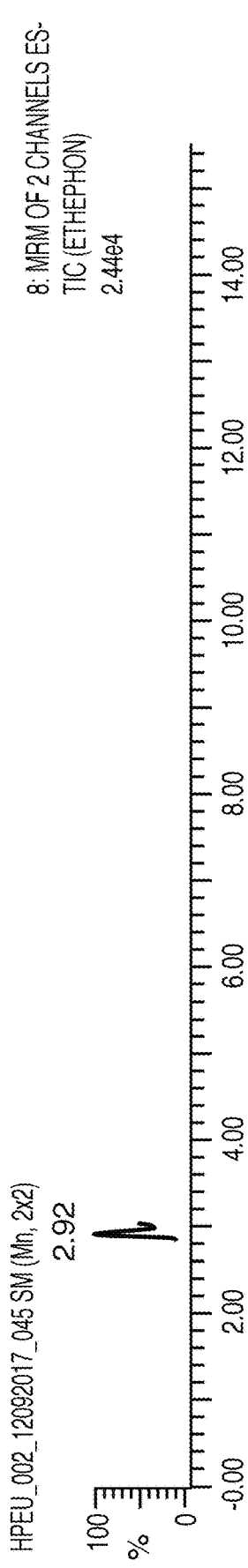
Figure 11J:
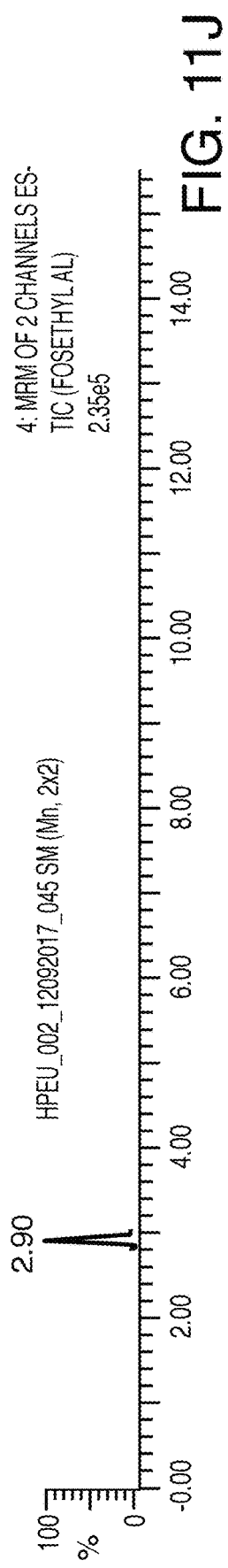
Figure 11K:
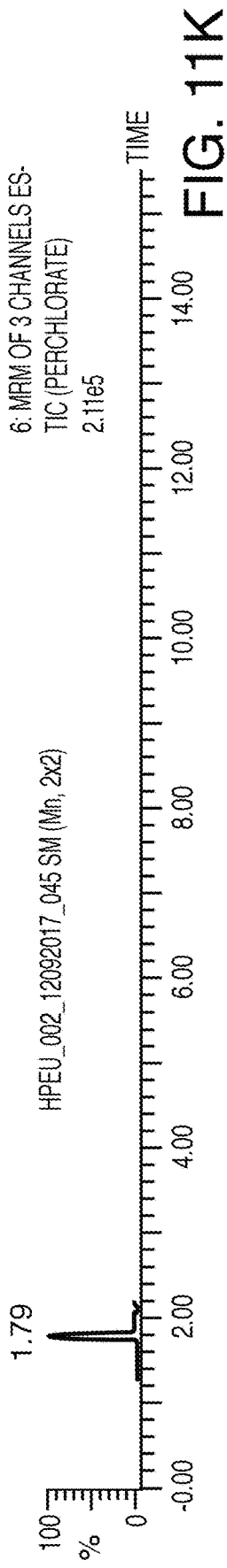
Figure 11L:
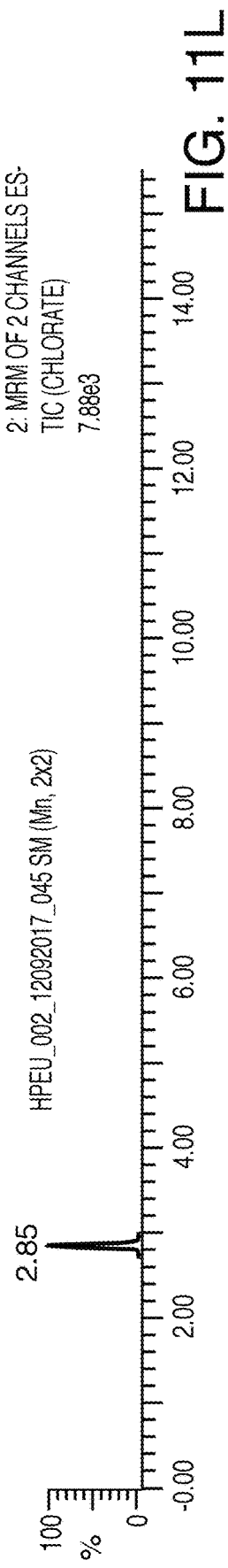
Figure 11M:
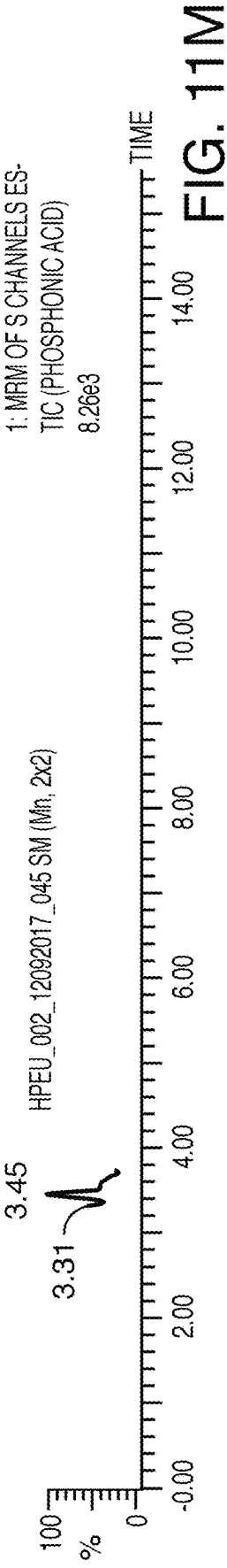
Figure 12D:
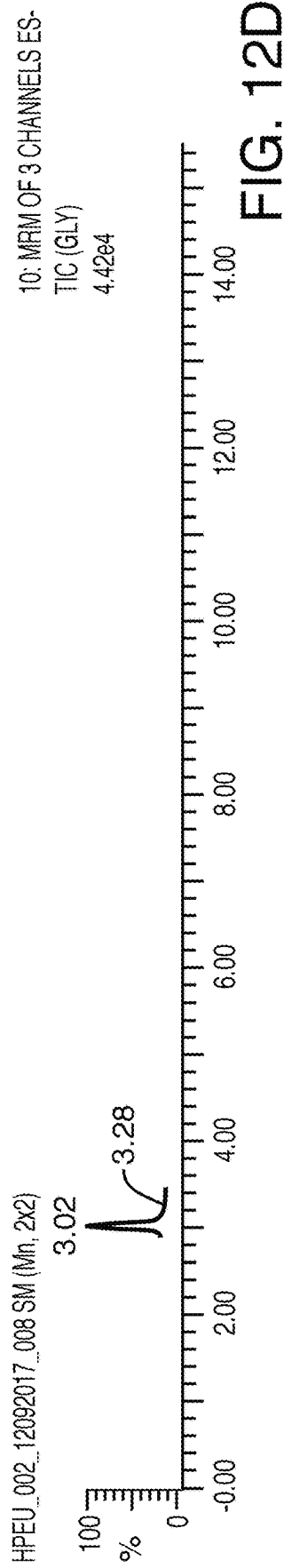
Figure 12E:
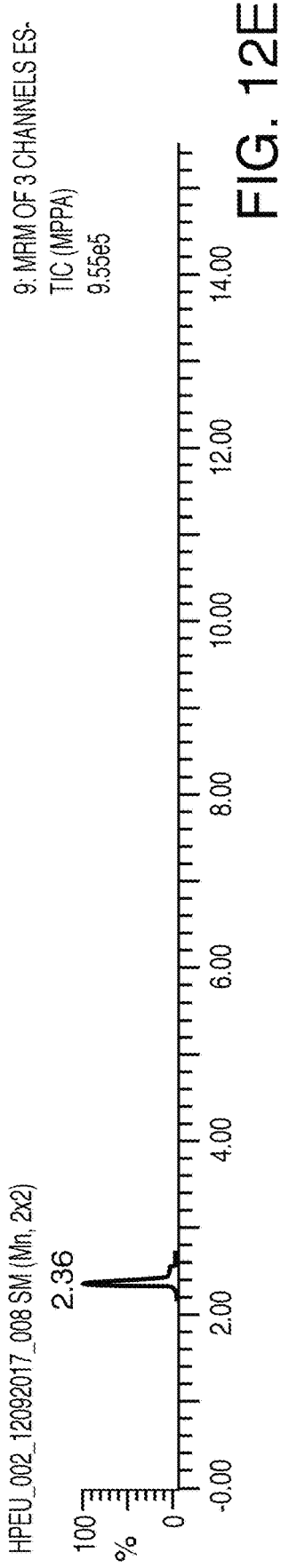
Figure 12F:
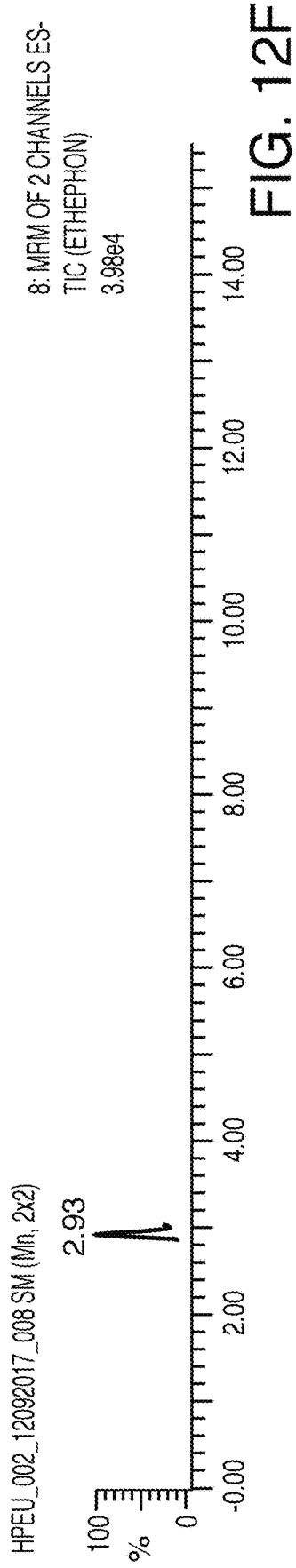
Figure 12J:
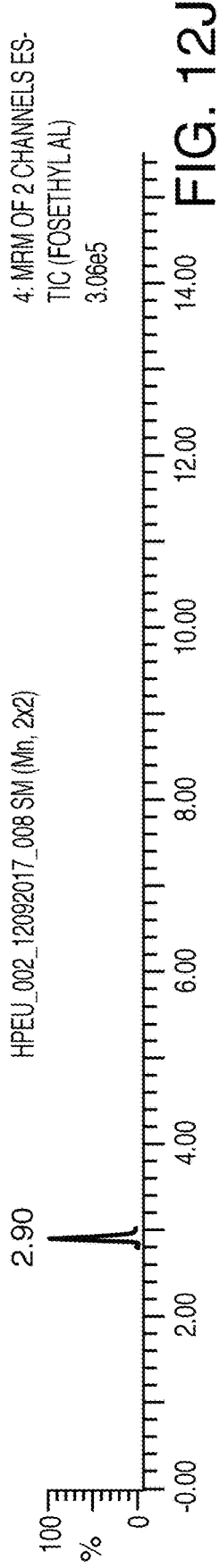
Figure 12K:
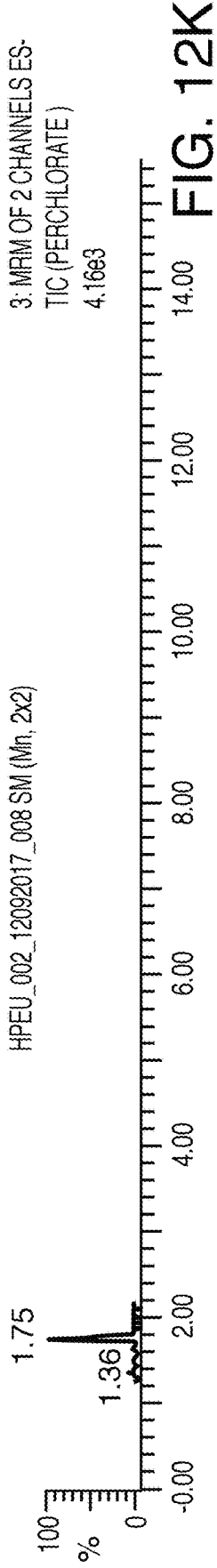
Figure 12L:
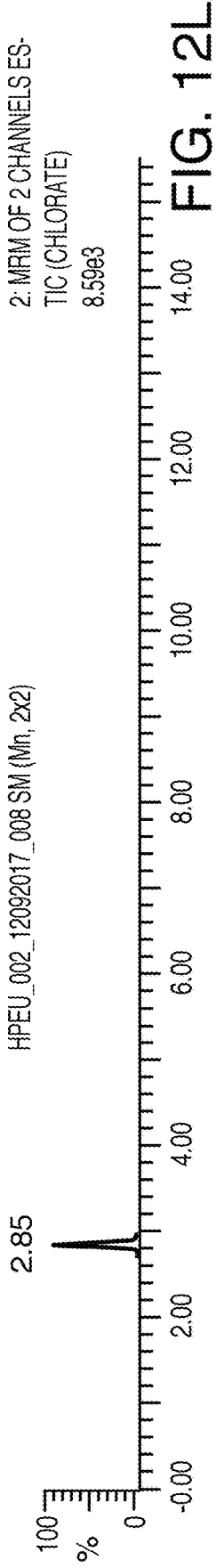
Figure 12M:
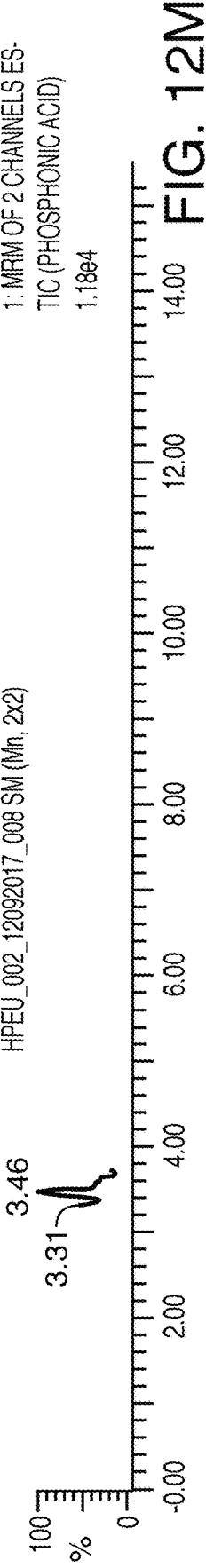
Figures 13A, 13B, 13C:
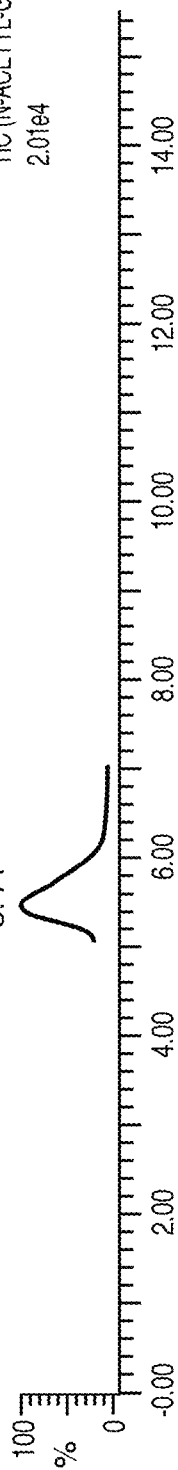
Figure 13D:
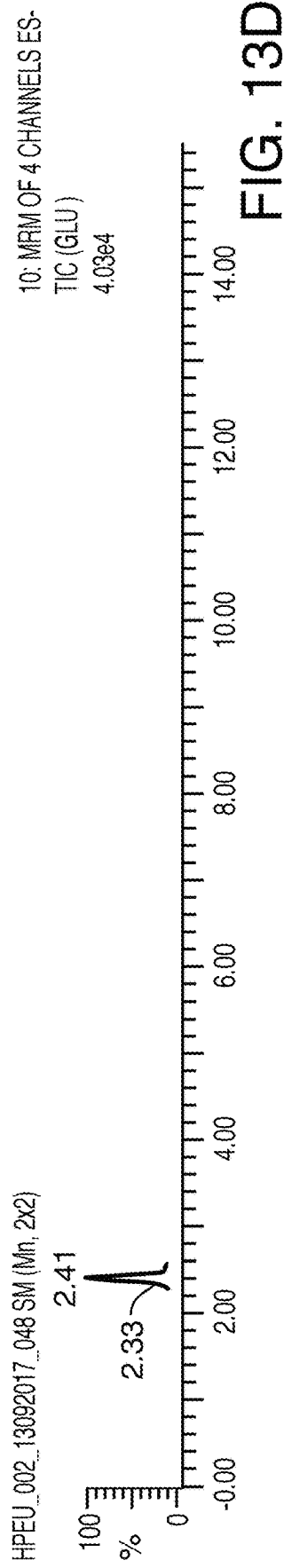
Figure 13E:
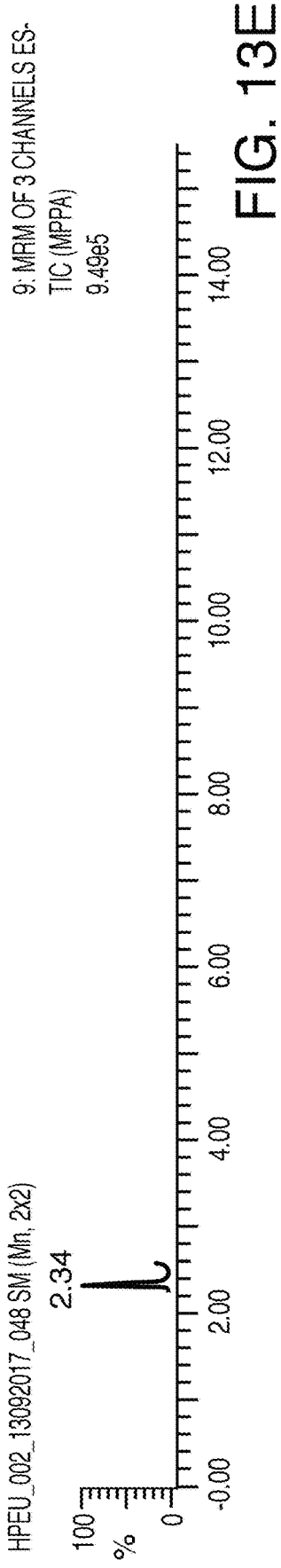
Figure 13F:
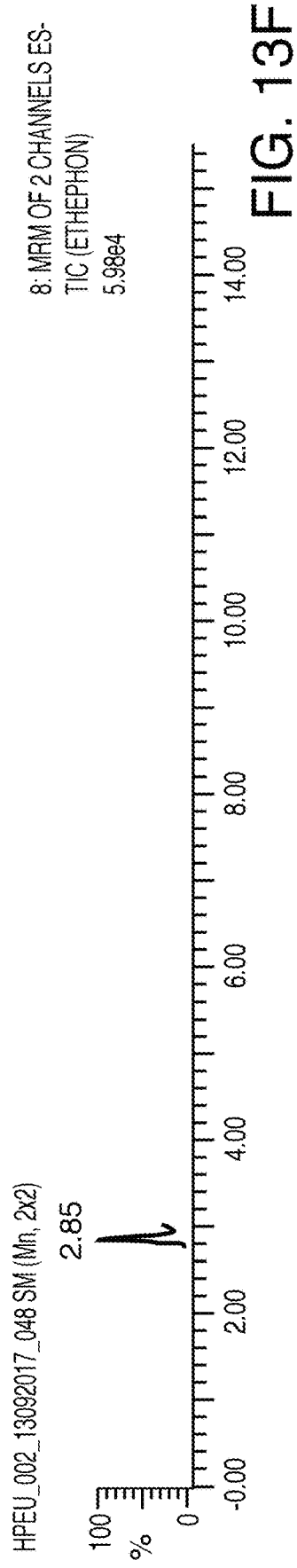
Figure 13J:
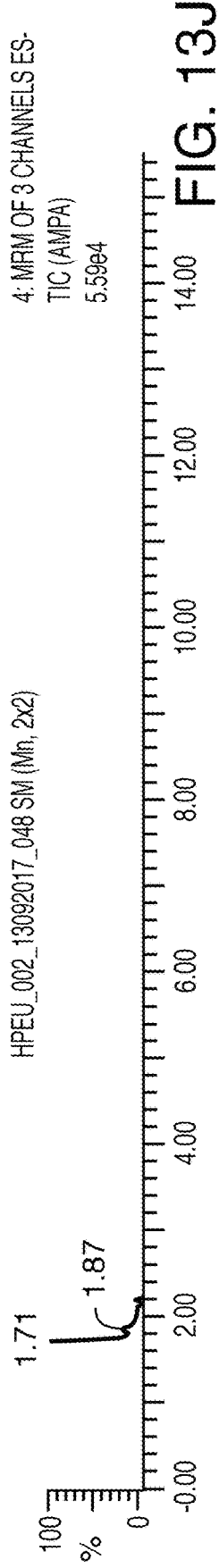
Figure 13K:
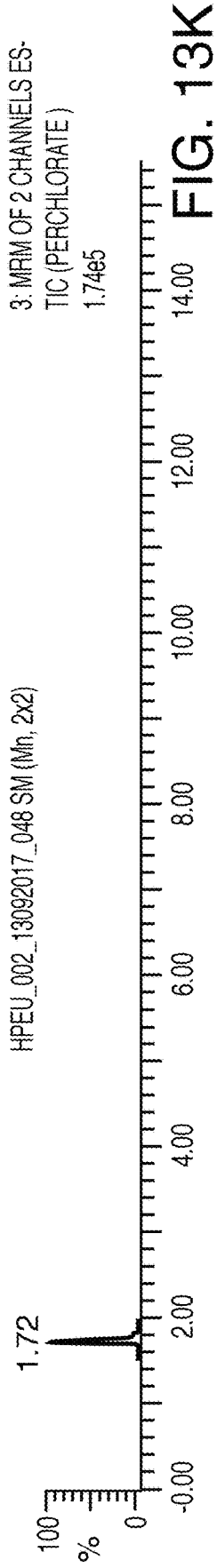
Figure 13L:
Figure 13M:
Figure 14A:
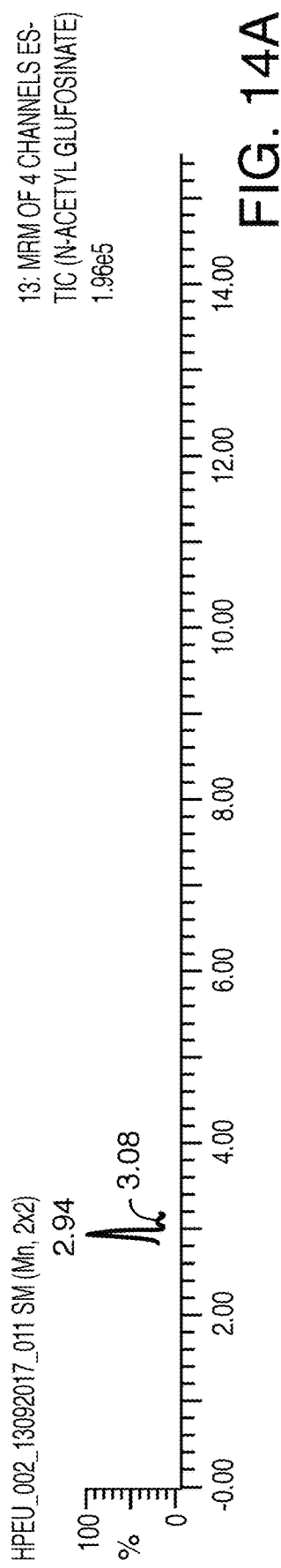
Figure 14B:
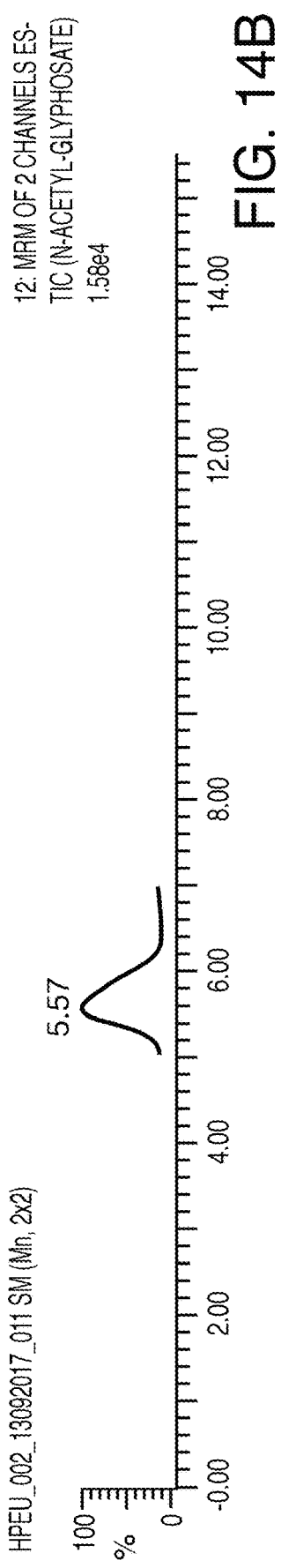
Figure 14C:
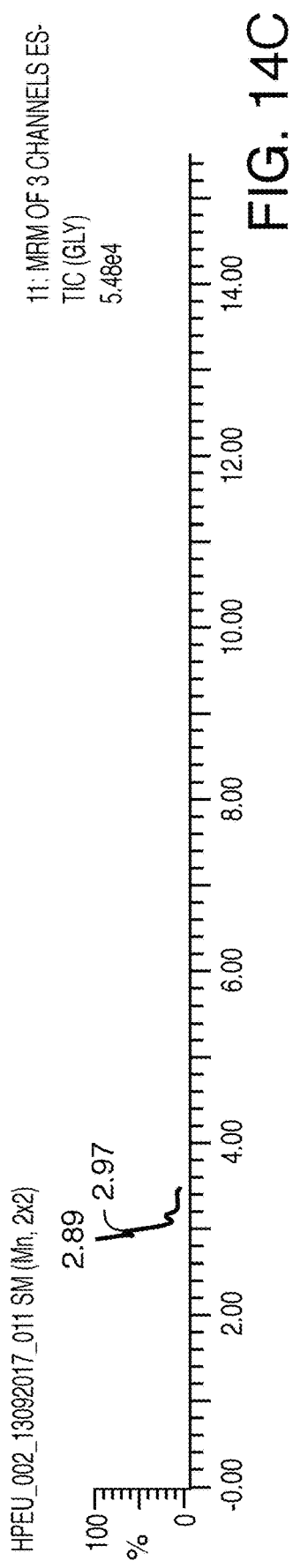
Figure 14D:
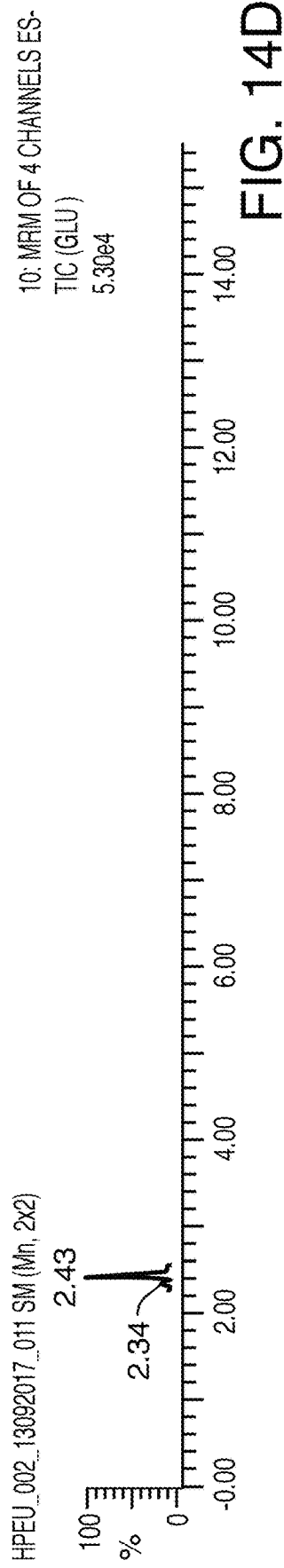
Figure 14E:
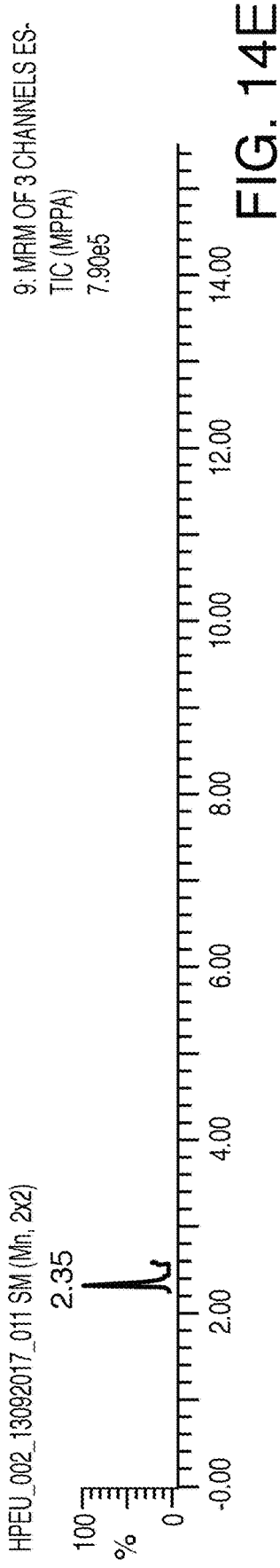
Figure 14F:
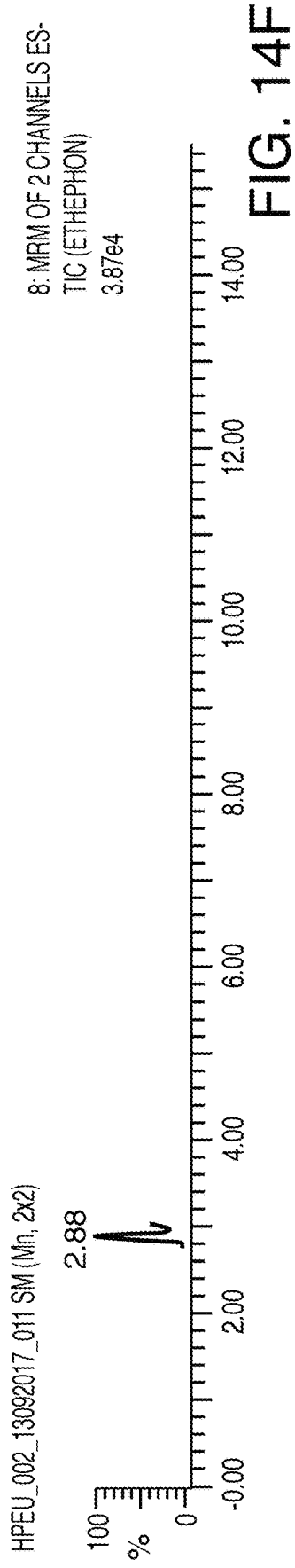
Figure 14J:
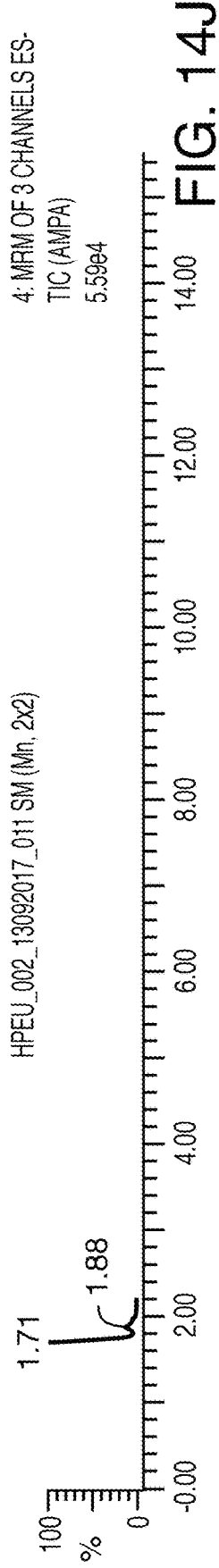
Figure 14K:
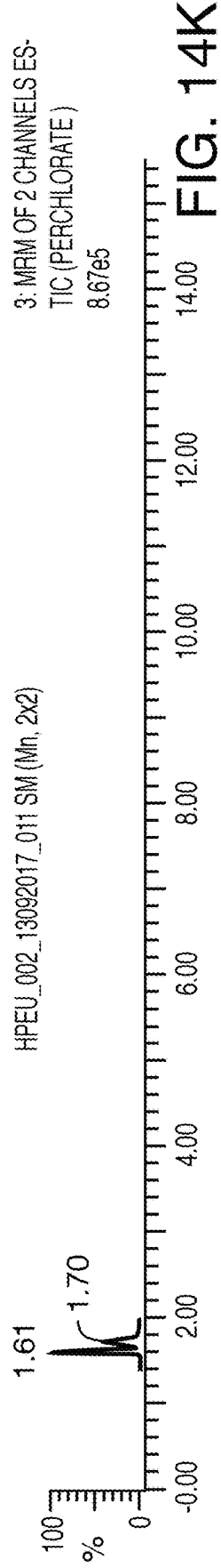
Figure 14L:
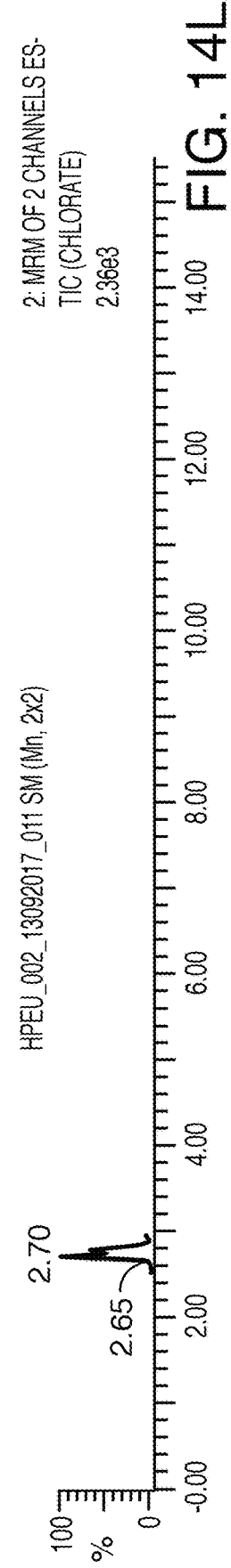
Figure 14M:

Six batches of Torus DEA columns were evaluated to determine repeatability of the method across batch lots, focusing on AMPA, glyphosate and glufosinate. Replicate injections (n=6) were made on all six columns. Representative results are summarized in FIG. 10, where one injection per column is overlaid. Excellent reliability was achieved for all injections across the six batches, in terms of retention time (<0.12 minute difference) and peak area (% RSD<20%)

Conclusions. Expanding on previous LC-MS/MS methods, initial work using the Torus DEA column has demonstrated excellent performance for the reliability analysis of anionic polar pesticides in food. The key benefits include (i) improved chromatographic performance for a broad scope of anionic pesticides in a single injection; (ii) maintained system sensitivity with LODs<0.001 mg/kg for all analytes; (iii) repeatable quantitative analysis, with % RSD<22% achieved at 0.01 mg/kg in onion and spinach, without isotopically labelled internal standards; (iv) excellent repeatability across 6 batches of Torus DEA columns, where retention times were <0.05 minute intra-batch and <0.12 minute inter-batches for AMPA, glyfosinate and glyphosate; and (v) incurred residues of analytes accurately quantified using standard addition calibration, in the absence of isotopically labelled internal standard.

Example 4

Polar pesticides in onion and spinach were determined using the methodology of the present disclosure. The following polar pesticides were tested: glyphosate, AMPA, glufosinate, perchlorate, ethephon, fosetyl-aluminium, maleic hydrazide, phosphonic acid, chlorate, N-acetyl glyphosate, N-acetyl glufosinate, ethephon hydroxyl, MPPA. A sample of onion and spinach was spiked at various levels and left at room temperature for 2 hours. The sample was then extracted using both the QuPPe and a modified QuPPe extraction method. For the QuPPe extraction method, a 5 g portion of sample was acidified with 5 mL of 1% formic acid in MeOH. For the modified QuPPe extraction method a 5 g portion of sample was acidified with 5 mL of acetonitrile. For both the QuPPe and modified QuPPe extraction methods, the resulting mixture was vortex for 2 min, and centrifuged for 5 minutes at 6000 rpm. The mixture was then filtered with a 0.25 micron filter and then introduced to the chromatography system. Except for the difference in extraction solvent noted above, the QuPPe and the modified QuPPE extraction methods are the same.

MS conditions are shown in Table 12, where quantification traces are indicated in bold. The capillary voltage is 2.4 kV, the source temperature is 150° C., the desolvation temperature is 600° C., the cone gas flow is 300 L/Hr, the nebulizer is 7 bar, and the threshold ESI Neg is 40.

TABLE 12

Example 4 MS Conditions (Quantification traces indicated in bold)

| Compound | Ion Mode | Transitions | Cone Voltage (V) | Collision Energy (eV) |
|---|---|---|---|---|
| Glyphosate | ESI− | 167.75 > 62.80 | 15 | 15 |
| | | 167.75 > 80.80 | | 15 |
| | | 167.75 > 149.85 | | 10 |
| AMPA | ESI− | 109.50 > 62.80 | 15 | 15 |
| | | 109.50 > 78.80 | | 15 |
| | | 109.50 > 80.80 | | 10 |
| Glufosinate | ESI− | 179.80 > 62.80 | 15 | 25 |
| | | 179.80 > 84.85 | | 17 |
| | | 179.80 > 134.00 | | 16 |
| Chlorate | ESI− | 82.45 > 66.80 | 15 | 14 |
| | | 82.45 > 50.80 | | 15 |
| Ethephon (Soft ionization ON) | ESI− | 142.65 > 78.75 | 15 | 13 |
| | | 142.65 > 106.85 | | 8 |
| Fosethyl Aluminum | ESI− | 108.50 > 62.80 | 15 | 16 |
| | | 108.50 > 80.80 | | 10 |
| Phosphonic acid | ESI− | 80.40 > 62.80 | 15 | 15 |
| | | 80.40 > 78.80 | | 10 |
| Maleic hydrazyde | ESI− | 110.50 > 54.85 | 15 | 14 |
| | | 110.50 > 81.80 | | 14 |
| | | 110.50 > 82.80 | | 12 |
| Perchlorate | ESI− | 98.75 > 66.90 | 20 | 45 |
| | | 98.75 > 82.85 | | 18 |
| Ethephon Hydroxy | ESI− | 124.60 > 78.80 | 15 | 14 |
| | | 124.60 > 94.80 | | 12 |
| | | 124.60 > 106.90 | | 11 |
| MPPA | ESI− | 150.70 > 62.80 | 15 | 25 |
| | | 150.70 > 106.85 | | 16 |
| | | 150.70 > 132.85 | | 12 |
| N-Acetyl-Glyphosate | ESI− | 209.80 > 149.90 | 15 | 12 |
| | | 209.80 > 191.90 | | 11 |
| N-Acetyl-Glufosinate | ESI− | 221.90 > 58.90 | 20 | 14 |
| | | 221.90 > 135.90 | | 20 |
| | | 221.90 > 161.90 | | 12 |

TABLE 13

Example 4 Mobile Phase Gradient

| Time (Min) | First Solvent (%) | Second Solvent (%) | Curve |
|---|---|---|---|
| 0 | 10 | 90 | |
| 4.5 | 60 | 40 | 2 |
| 8.5 | 60 | 40 | 6 |
| 20 | 10 | 90 | 1 |

The chromatography system included an ACQUITY® UPLC® system commercially available from Waters Corporation, Milford, Mass., USA. The column was a TORUS® DEA column, 2.1×100 mm, 130 Angstroms, 1.7 micron particle, commercially available from Waters Corporation, Milford, Mass., USA. The LC system was an ACQUITY® I class (FTN). The detector was a Xevo® TQ-XS detector, commercially available from Waters Corporation, Milford, Mass., USA. Solvent A is 50 mM Ammonium Formate pH 2.9 (0.9% Formic Acid) and Solvent B is MeCN+0.9% Formic Acid. The column temperature is 50° C. and the sample temperature is 10° C. The injection volume is 10 μL and the flow rate is 0.5 mL/min.

The chromatograms for the QuPPE and modified QuPPE for 10 ppb post spike for onion extract are shown in FIGS. 11A-11M and 12A-12M, respectively.

The repeatability of the onion extract can be seen in Table 14 at two concentration levels, n=5. As can be seen in Table 14, maleic hydrazide incurred residue and AMPA had matrix suppression.

TABLE 14

Example 4 repeatability of Onion Extract

| Compound | Conc level (ppb) | Number of samples | QuPPE Mean (ppb) | QuPPE RSD (%) | Mod. QuPPE Mean (ppb) | Mod. QuPPE RSD (%) |
|---|---|---|---|---|---|---|
| N-Acetyl-Glufosinate | 10 | 5 | 10.1 | 5.7 | 10.6 | 4.6 |
| | 50 | | 47.7 | 4.9 | 49.5 | 3.7 |
| N-Acetyl-Glyphosate | 10 | 5 | 10.2 | 8.8 | 10.1 | 7.3 |
| | 50 | | 49.9 | 3.4 | 47.3 | 2.1 |
| Glufosinate | 10 | 5 | 10.1 | 8.0 | 9.8 | 2.9 |
| | 50 | | 51.2 | 2.9 | 47.7 | 2.2 |
| Glyphosate | 10 | 5 | 9.7 | 9.3 | 9.2 | 6.2 |
| | 50 | | 44.8 | 0.8 | 48.3 | 4.1 |
| MPPA | 10 | 5 | 9.8 | 5.1 | 10.4 | 2.7 |
| | 50 | | 48.9 | 2.6 | 49.5 | 1.9 |
| Ethephon | 10 | 5 | 11.1 | 9.9 | 11.0 | 4.3 |
| | 50 | | 48.9 | 3.3 | 49.8 | 0.7 |
| Maleic hydrazyde | 200 | 5 | 249.1 | 12.0 | 205.2 | 4.0 |
| | 500 | | 445.6 | 10.5 | 492.8 | 1.1 |
| Fosethyl Aluminum | 10 | 5 | 10.0 | 8.1 | 9.9 | 7.4 |
| | 50 | | 50.5 | 4.1 | 47.2 | 3.3 |
| AMPA | 10 | 5 | / | / | / | / |
| | 50 | | | | | |
| Perchlorate | 10 | 5 | 8.5 | 17.9 | 11.0 | 4.7 |
| | 50 | | 50.8 | 19.2 | 37.2 | 7.3 |
| Chlorate | 10 | 5 | 9.6 | 9.1 | 10.3 | 9.9 |
| | 50 | | 50.3 | 6.5 | 53.5 | 1.6 |
| Ethephon Hydroxy | 10 | 5 | 9.5 | 8.3 | 9.2 | 4.2 |
| | 50 | | 51.8 | 4.2 | 47.5 | 5.3 |
| Phosphonic acid | 10 | 5 | 9.1 | 8.6 | 10.9 | 7.8 |
| | 50 | | 47.5 | 2.3 | 51.6 | 4.4 |

The chromatograms for the QuPPE and modified QuPPE for 10 ppb post spike for spinach extract are shown in FIGS. 13A-13M and 14A-14M, respectively.

The repeatability of the spinach extract can be seen in Table 15 at two concentration levels, n=5. As can be seen in Table 15, phosphonic acid incurred residue.

TABLE 15

Example 4 Repeatability of Spinach Extract

| Compound | Conc level (ppb) | Number of samples | QuPPE Mean (ppb) | QuPPE RSD (%) | Mod. QuPPE Mean (ppb) | Mod. QuPPE RSD (%) |
|---|---|---|---|---|---|---|
| N-Acetyl-Glufosinate | 10 | 5 | 10.4 | 3.8 | 15.1 | 4.2 |
| | 50 | | 49.0 | 1.1 | 64.0 | 3.2 |
| N-Acetyl-Glyphosate | 10 | 5 | 11.4 | 3.8 | 11.6 | 3.7 |
| | 50 | | 50.9 | 2.2 | 51.9 | 1.9 |
| Glufosinate | 10 | 5 | 12.8 | 3.3 | 11.7 | 7.6 |
| | 50 | | 52.5 | 2.4 | 51.0 | 1.9 |
| Glyphosate | 10 | 5 | 10.4 | 7.3 | 9.9 | 3.8 |
| | 50 | | 52.5 | 4.5 | 48.2 | 3.0 |
| MPPA | 10 | 5 | 12.4 | 2.3 | 14.0 | 2.0 |
| | 50 | | 56.5 | 5.1 | 60.7 | 3.4 |
| Ethephon | 10 | 5 | 11.1 | 3.4 | 12.8 | 5.0 |
| | 50 | | 46.1 | 2.6 | 57.4 | 4.5 |
| Maleic hydrazyde | 10 | 5 | 12.7 | 5.4 | 9.9 | 5.2 |
| | 50 | | 60.9 | 5.4 | 49.5 | 7.0 |
| Fosethyl Aluminum | 10 | 5 | 11.0 | 3.1 | 11.8 | 1.2 |
| | 50 | | 51.8 | 2.3 | 53.1 | 2.1 |
| AMPA | 10 | 5 | 10.1 | 3.3 | 7.9 | 6.7 |
| | 50 | | 44.8 | 4.2 | 33.4 | 4.7 |
| Perchlorate | 10 | 5 | 9.3 | 6.7 | 6.4 | 12.5 |
| | 50 | | 47.3 | 1.1 | 49.5 | 3.9 |
| Chlorate | 10 | 5 | 11.4 | 7.6 | 11.3 | 5.4 |
| | 50 | | 52.5 | 5.0 | 59.3 | 1.7 |
| Ethephon Hydroxy | 10 | 5 | 10.36 | 3.1 | 10.2 | 5.0 |
| | 50 | | 49.2 | 3.1 | 50.0 | 0.5 |
| Phosphonic acid | 10 | 5 | 162.9 | 11.1 | 306.0 | 3.7 |
| | 50 | | 91.7 | 10.5 | 310.9 | 2.7 |

As shown in the above examples, improved chromatography (peak shapes) and robustness for the Torus DEA solution using optimized method conditions including (i) 0.9% formic acid added to solvent B MeCN (generated better peak shapes); (ii) 10:90 initial condition (separates Fos A1 and AMPA); (iii) curve type 2 (improved AMPA peak shape); and (iv) 60:40 final condition (more stable elution). Acceptable linearity for onion and spinach extracts using both QuPPE and modified QuPPE extraction solvents. Acceptable accuracy and precision for pre-spikes extraction solvent and onion extracts. Spinach extracts demonstrates precise results but inaccurate for a few. The most promising results were obtained with QuPPE solvent. As can be seen from the above examples, AMPA is heavily suppressed in onion matrix.

Example 5

The methods of the present technology can be used with various detectors (e.g., mass spectrometers), probes, and columns. This example shows how the QuPPE extraction method can be used to separate seven compounds (Glufosinate, Glyphosate, Ethephon, AMPA, Fosetyl aluminum, Chlorate, and phosphonic acid), and in particular to separate chlorate and perchlorate from a fruit sample, for example, a grape sample, The system used for the separation includes an ACQUITY® I-Class (FL) with a Xevo TQ-S micro detector. The column is a TORUS DEA 2.1×50 mm, 1.7 The mobile phases are: Mobile Phase A: LCMS Grade 50 mM ammonium formate having a pH of 2.9 (formic acid); and Mobile Phase B: LCMS Grade acetonitrile 0.9% formic acid. The flow rate is 0.50 mL/min. The pose injection gradient delay is 320 µl and the injection volume is 18 µl (20 µl loop installed). The gradient is shown in Table 15. The XEVO TQ-X Micro operates at a source temperature of 150° C. and a pin voltage of 0.5 kV. The desolvation temperature is 600° C. and the cone gas flow is 150 L/hr. The desolvation gas flow is 1000 L/hour. The data was collected in ESI (−) and US (−).

TABLE 15

Example 5 Mobile Phase Gradient

| Time (Min) | Solvent A (%) | Solvent B (%) | Curve |
|---|---|---|---|
| 0 | 10 | 90 | Initial |
| 2.00 | 80 | 20 | 4 |
| 4.25 | 80 | 20 | 6 |
| 7.80 | 10 | 90 | 1 |

Figure 15A:
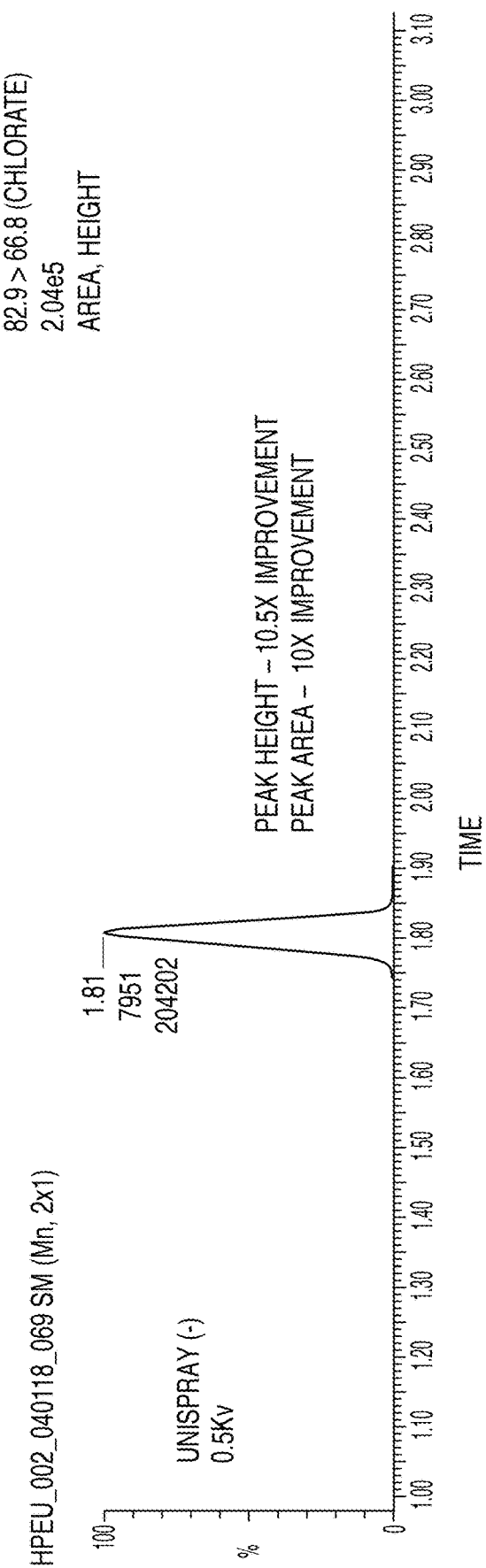
FIG. 15A shows a chromatogram with a UniSpray probe used at 0.5 kV
Figure 15B:
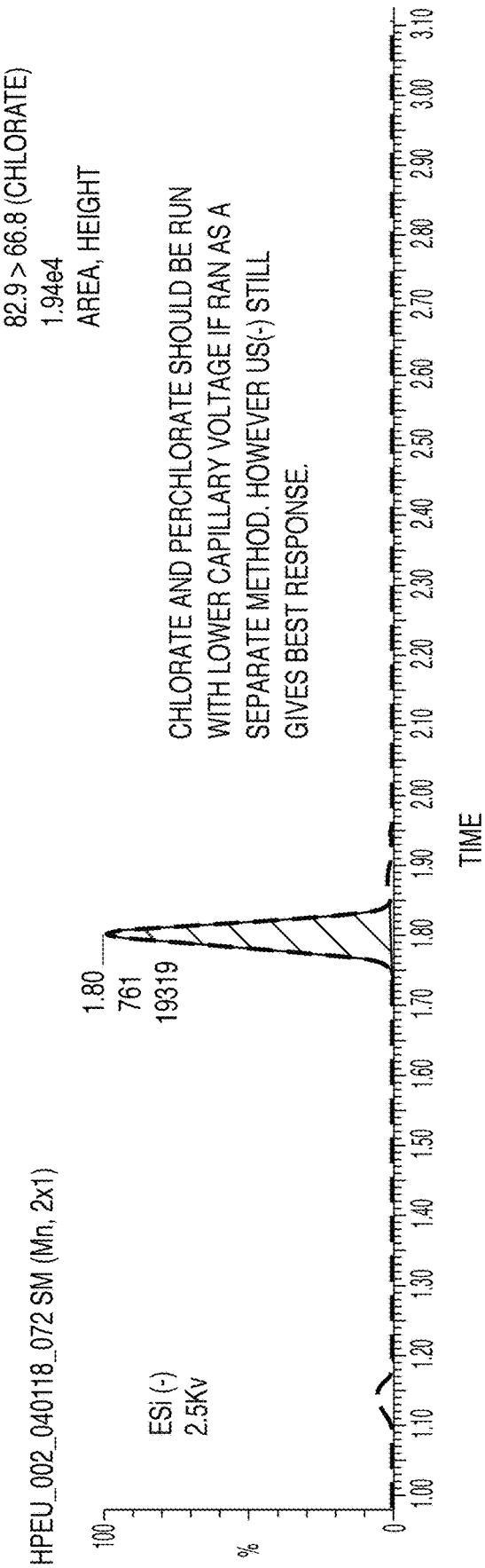
FIG. 15B shows a chromatogram with an ESI (−) probe at 2.5 kV for the detection of chlorate in the grape sample, according to an illustrative embodiment of the technology.

A sample of grape was spiked with 100 ppb of chlorate and perchlorate in a manner similar to the above examples. FIG. 15A shows a chromatogram with a UniSpray probe used at 0.5 kV and FIG. 15B shows a chromatogram with an ESI (−) probe at 2.5 kV for the detection of chlorate in the grape sample. The use of the UniSpray probe results in a 10.5 times improvement in peak height and a ten times improvement in peak area. Similar improvements were seen for perchlorate in the grape sample.

While this disclosure has been particularly shown and described with reference to example embodiments thereof, it will be understood by those skilled in the art that various changes in form and details may be made therein without departing from the scope of the invention encompassed by the appended claims.

We claim:

1. A chromatography method for determining at least one polar pesticide or metabolite, the method comprising:
   (i) obtaining a sample containing at least one polar pesticide or metabolite in a sample matrix;
   (ii) introducing the sample to a chromatography system comprising a column having a reverse phase stationary phase material contained inside the column, wherein the reverse phase stationary phase material comprises inorganic/organic hybrid particles, a diol functional group, and an amine functional group, wherein the ratio of amine functional group to diol functional group is between about 0.01:1 and 1:1, and wherein the reverse phase stationary phase material is configured to operate under a pressure at or above 1,000 psi;
   (iii) flowing the sample with a mobile phase eluent through the column, wherein the at least one polar pesticide or metabolite is substantially resolved and retained; and
   (iv) detecting the at least one polar pesticide or metabolite using a detector.

2. The method of claim 1, wherein the sample contains at least 2 polar pesticides or metabolites and the at least 2 polar pesticides or metabolites are substantially resolved and retained.

3. The method of claim 1, further comprising extracting the at least one polar pesticides or metabolite from the sample matrix before introducing the extracted sample to the chromatography system.

4. The method of claim 1, wherein the at least one polar pesticide or metabolite is selected from the group consisting of Ethephon, Glufosinate-ammonium, Glyphosate, Fosetyl-aluminum, Phosphonic acid, Maleic hydrazide, Perchlorate, Chlorate, Cyromazine, Amitrole, Daminozide, Ethylenethiorea, Propylenethiourea, Chlormequat, Mepiquat, Diquat, Paraquar, and metabolites thereof, and combinations thereof.

5. The method of claim 1, wherein the amine functional group comprises a diethyl amine functional group, a 2-picoylamine functional group, a 2-ethylpyridine functional group, or a 4-ethylpyridine functional group.

6. The method of claim 1, wherein the mobile phase eluent comprises acetonitrile, buffer or combinations thereof.

7. The method of claim 1, wherein the mobile phase eluent has a flow rate between 0.2 and 1.0 mL/min.

8. The method of claim 1, wherein the mobile phase eluent comprises organic and aqueous solvents containing buffer, or combinations thereof, and wherein the at least one polar pesticide or metabolite is eluted using a gradient elution, the elution comprising a gradient of a first solvent comprising an aqueous solvent and a second solvent comprising an organic solvent.

9. The method of claim 1, wherein the column temperature is between 30 and 60° C.

10. The method of claim 1, wherein the method repeatability of performing the method of claim 1 at least 10 times using the same chromatography system measuring peak area has a Relative Standard Deviation (RSD) of less than about 20%, wherein the sample is a solution of polar pesticide or metabolite reference standards.

11. The method of claim 1, wherein the sample contains at least 2 polar pesticides or metabolite which are substantially resolved, and wherein the substantially resolved at least 2 polar pesticides or metabolites have a resolution greater than 1.

12. The method of claim 1, wherein the detector is selected from the group consisting of a UV/VIS detector, PDA detector, fluorescence detector, mass spectrometer, refractive index detector, evaporative light scattering detector and a charged aerosol detection.

13. The method of claim 1, wherein the amine functional group is a diethyl amine functional group.

14. The method of claim 1, wherein the retention time for the at least one polar pesticide or metabolite is at least twice the retention time corresponding to the void volume of the column.

15. The method of claim 8, wherein:
the first solvent is 50 mM ammonium formate in water, adjusted to pH 2.9 with formic acid; and
the second solvent is 0.9% formic acid in acetonitrile.

16. The method of claim 15, wherein the gradient comprises an initial ratio of the first solvent to the second solvent of 10:90, increasing to a ratio of the first solvent to the second solvent of 60:40 over a first period of time.

17. The method of claim 16, wherein the first period of time is 4.5 minutes.

18. The method of claim 16, further comprising continuing the elution at the 60:40 ratio of the first solvent to the second solvent for a second period of time.

19. The method of claim 1, further comprising:
(v) washing the column with an aqueous solution of 0.5 to 10 mM citric acid, followed by washing the column with a solution of formic acid in acetonitrile.

20. The method of claim 1, wherein the at least one polar pesticide is anionic.

* * * * *